US008992945B2

(12) United States Patent
Lee et al.

(10) Patent No.: US 8,992,945 B2
(45) Date of Patent: Mar. 31, 2015

(54) SUPRAMACROMOLECULAR POLYMER COMPLEXES PROVIDING CONTROLLED NITRIC OXIDE RELEASE FOR HEALING WOUNDS

(75) Inventors: Ping I. Lee, Toronto (CA); Yan Li, Hangzhou (CN)

(73) Assignee: University of Toronto (CA)

( * ) Notice: Subject to any disclaimer, the term of this patent is extended or adjusted under 35 U.S.C. 154(b) by 867 days.

(21) Appl. No.: 12/675,498

(22) PCT Filed: Aug. 20, 2008

(86) PCT No.: PCT/CA2008/001484
§ 371 (c)(1),
(2), (4) Date: Feb. 26, 2010

(87) PCT Pub. No.: WO2009/026680
PCT Pub. Date: Mar. 5, 2009

(65) Prior Publication Data

US 2010/0303891 A1 Dec. 2, 2010

(30) Foreign Application Priority Data

Aug. 27, 2007 (CA) ..................................... 2599082

(51) Int. Cl.

| | |
|---|---|
| ***A61K 9/00*** | (2006.01) |
| ***A61K 9/70*** | (2006.01) |
| ***C08G 69/48*** | (2006.01) |
| ***A61K 31/765*** | (2006.01) |
| ***A61K 31/785*** | (2006.01) |
| ***A61K 47/48*** | (2006.01) |
| ***A61L 15/44*** | (2006.01) |
| ***A61L 29/16*** | (2006.01) |
| ***A61L 31/16*** | (2006.01) |
| ***C08L 39/08*** | (2006.01) |
| *C08L 35/02* | (2006.01) |

(52) U.S. Cl.
CPC ......... *A61K 31/785* (2013.01); *A61K 47/48176* (2013.01); *A61L 15/44* (2013.01); *A61L 29/16* (2013.01); *A61L 31/16* (2013.01); *A61L 2300/114* (2013.01); *C08L 35/02* (2013.01); *C08L 39/08* (2013.01)
USPC ....... 424/400; 424/443; 424/78.37; 427/2.31; 525/54.1

(58) Field of Classification Search
CPC ........... A61K 31/785; A61K 47/48176; A61L 15/44; A61L 29/16; C08L 35/02
See application file for complete search history.

(56) References Cited

U.S. PATENT DOCUMENTS 5,770,645 A * 6/1998 Stamler et al. ................ 524/419
6,255,277 B1 * 7/2001 Stamler et al. ................ 424/484
2002/0002353 A1 * 1/2002 Michal et al. ................. 604/265
2002/0094985 A1 * 7/2002 Herrmann et al. ............ 514/245
2003/0236514 A1 12/2003 Schwarz
2009/0081279 A1 * 3/2009 Jezek et al. ................... 424/445
2010/0112033 A1 * 5/2010 Ganzarolli de Oliveira et al. ............................. 424/425

FOREIGN PATENT DOCUMENTS

EP 1004294 A1 * 5/2000

OTHER PUBLICATIONS

Popescu, I., et al;., "Biomedical Applications of Maleic Anhydride Copolymers", 2011, Rev., Roum., Chim., 56, pp. 173-188.*
Hao, J.S. et al. "Complexation Between PVP and Gantrez Polymer and Its Effect on Release and Bioadhesive Properties of the Composite PVP/Gantrez Films" 2004, Pharmaceutical Development and Technology, 9, pp. 379-386.*
Seabra, A.B., et al., "Solid Films of Blended Poly(Vinyl Alcohol)/ Poly (Vinyl Pyrrolidone) for Topical S-Nitrosoglutathione and Nitric Oxide Release", 2005, Journal of Pharmaceutical Sciences, 94, pp. 994-1003.*

(Continued)

*Primary Examiner* — Michael G Hartley
*Assistant Examiner* — Lance Rider
(74) *Attorney, Agent, or Firm* — Price Heneveld LLP

(57) ABSTRACT

A bio-adhesive supramacromolecular complex of the general formula:

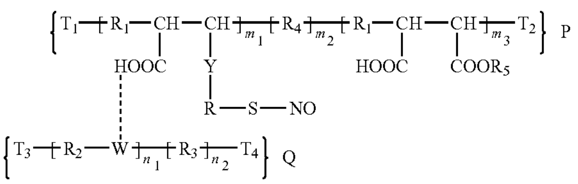

wherein $R_1$ is independently selected from the group consisting of an alkane unsubstituted or substituted with alkoxy groups; $R_2$ is independently selected from the group consisting of C1-6 alkyl; $R_3$ and $R_4$ are independently selected from the group consisting of optionally substituted aliphatic or aromatic alkyl; $R_5$ is independently selected from the group consisting of H or C1-6 alkyl; W is a hydrogen-bond accepting functional group-containing entity; Y is a carboxylic acid ester or amide linkage; R is an independently selected peptide linking group; $T_1$, $T_2$, $T_3$ and $T_4$ are independently selected polymer residues; and $m_1$, $m_2$, $m_3$, $n_1$ and $n_2$ are integers selected from at least 25; and wherein P has a molecular weight of about $1\times10^3$ to $1\times10^7$ and Q has a molecular weight of about $1\times10^3$ to $1\times10^7$. The complex provides controlled nitric oxide release over a longer period of time than prior art compounds in the locally delivery systems. Novel compositions, methods of preparation, apparatus including layer-by-layer assemblies coating, electrospinning and ultrasonic atomization, skin coverings containing and medical use of the complexes are described.

18 Claims, 16 Drawing Sheets

(56) References Cited

OTHER PUBLICATIONS

Pato, J., et al., "Polymeric Prodrugs, 1 Synthesis by Direct Coupling of Drugs", 1982, Makromol. Chern., Rapid Comrnun, 3, pp. 643-647.*
Chourasia, M.K., et al., "Pharmaceutical Approaches to Colon Targeted Drug Delivery Systems", 2003, J Pharm Pharmaceut Sci , 6, pp. 1-51.*
Arbos, P. et al., "G antrez AN as a new polymer for the preparation of ligand-nanoparticle conjugates", 2002, J. Controlled Release, 82, pp. 321-330.*
Gomez S, Gamazo C, San Roman B et al. Development of a novel vaccine delivery system based on Gantrez nanoparticles. J. Nanosci. Nanotechnol.6, pp. 3283-3289 (2006).*
Wei., J., et al., "Diastereoselective Synthesis of ç-Lactams by a One-Pot, Four-Component Reaction". Organic Letters, 2007, pp. 4077-4080.*
Butler, P.J.G., et al., "The Use of Maleic Anhydride for the Reversible Blocking of Amino Groups in Polypeptide Chains", 1969, Biochem J., pp. 679-689.*
Translation of the Examiner's Comments, pp. 1-6, Mar. 5, 2009.

* cited by examiner (A)

(B)

SUPRAMACROMOLECULAR POLYMER COMPLEXES PROVIDING CONTROLLED NITRIC OXIDE RELEASE FOR HEALING WOUNDS

RELATED APPLICATIONS

This application claims priority from Canadian Patent Application no. 2,599,082, filed Aug. 27, 2007 entitled “Supramacromolecular Complexes Providing Controlled Nitric Oxide Release for Healing Wounds”, the content of which is incorporated herein by reference.

BACKGROUND OF THE INVENTION

Since the discovery that nitric oxide (NO) is identical to the elusive endothelium-derived relaxing factor [1], many more profound biological roles of NO have been identified and elucidated [2-6]. These findings prompted further exploration of potential applications of exogenous NO in wound healing, cardiovascular diseases, respiratory diseases, cancer therapy, nerve system reconstruction, as well as new functional medical devices. In this regarding, local delivery of NO has great potential in gaining clinical utility as evident in its demonstrated success in treating wound infection using topical applied NO gas [7]. However, the short half life of this small gaseous molecule and its intrinsic instability have presented great challenges for its incorporation into pharmaceutical dosage forms and drug delivery systems. It has been reported that NO endogenously synthesized by vascular endothelial cells has a very short biological half life of 5 sec or less [8, 9]. Because NO is rapidly scavenged by hemoglobin, its site of action in the tissue would be localized to where it is generated. The chemical instability of NO in cells and tissue has been attributed to its rapid oxidation to both $NO_2^-$ and $NO_3^-$.

Besides organic nitrates and sodium nitrite which are well known sources of NO, there are two other families of NO precursors which have been studied extensively. One consists of diazeniumdiolates and the other S-nitrosothiols. Diazeniumdiolates include compounds of structure $R_1R_2NN(O)=NOR_3$, which are also known as NONOates. Numerous efforts have been made in developing NO-releasing materials based on this class of NO donors [10, 11]. These include the incorporation of diazeniumdiolates into different polymeric matrices through either physical blends or covalent attachment to the polymer backbone or side chains. Related prior art approaches on diazeniumdiolates are described below.

In WO 2005/011575, WO 2005/07008, and WO 2006/058318, Smith disclosed NO releasing devices based on either ion exchange resins or polyethyleneimine (PEI) fibrous multilaminates in which diazeniumdiolate moieties are attached to the polymer matrix through either ionic or covalent bonding. Upon contacting such NO derived polymers with an activator such as water, hydrogen cation or ascorbic acid at the time of activation or application to the wound, local NO release can be generated. However, the duration of NO release from such systems is short, typically lasting only 0.5 to 3 hours from the ion exchange resin systems and at most one to two days from the fibrous multilaminate devices.

Meyerhoff and coworkers disclosed in U.S. Pat. No. 6,841,166 and US 2006/0008529, NO releasing polymeric materials for thromboresistant blood contacting devices based on hydrophobic polymers (such as silicone rubber, poly(vinyl chloride), polyurethanes, etc.) containing a discrete NO doner including diazeniumdiolate derivatized fumed silica, dispersed diazeniumdiolates or covalently linked diazeniumdiolates, together with an acidic activator and a plasticizer. During activation, water penetrates slowly into the hydrophobic polymer matrix resulting in a prolonged release of NO into the aqueous environment up to several days. These systems have also been tested as implantable grafts, catheters or coatings on biomedical devices for the delivery of NO for the treatment of cardiovascular restenosis and blood circulation disorders [12-15]. In addition to biocompatibility concerns, these extremely hydrophobic materials are not suitable for wound healing applications because of their poor water absorbency and poor bioadhesion at the wound site.

Moreover, one major limitation in the in vivo application of this class of NONOate donors is the potential toxicity of leachable diazeniumdiolates and their decomposition products, particularly nitrosoamines, as elucidated in U.S. Pat. No. 6,841,166. Prior art approaches mentioned above as well as in U.S. Pat. No. 6,703,046 had employed hydrophobic polymers to minimize such leaching. However, leaching can still occur from these polymers containing hydrophilic acidic additives and plasticizers. Additionally, one established diazeniumdiolate pro-drug, V-PYRRO/NO, has the potential of forming N-nitrosopyrrolidine, which is one of the most potent experimental hepatocarcinogens known [16]. Furthermore, diamine-based and polyethylenimine-based diazeniumdiolates released into aqueous medium have been shown to form measurable levels of nitrosamines, a known class of carcinogens [12]. Therefore the application of diazeniumdiolates in vivo, especially for wound healing, appears to be limited.

Another major class of NO donors is S-nitrosothiols, which are compounds having the generic structure of R—SNO. As important endogenous and exogenous sources of NO, RSNOs are widely distributed in vivo and have been shown to store, transport, and release nitric oxide in the mammalian body [17]. In addition, their ability to generate NO upon aqueous activation in physiological fluid is particularly advantageous for the local delivery of NO, targeting only to a specific tissue without having to achieve a systemic load. Among the various endogenous RSNOs, S-nitrosoglutathione (GSNO) has attracted significant attention due to its ease of synthesis through a spontaneous reaction between glutathione and sodium nitrite at room temperature and its ability to be isolated as a solid, [18]. However, the stability of these small molecular RSNOs is less than satisfactory as the S—NO bond is both thermally and photolytically labile, and susceptible to hemolytic cleavage leading to the spontaneous release of NO and its rapid inactivation, thus limiting their suitability for practical applications including wound healing.

de Oliveira and coworkers have physically incorporated S-nitrosoglutathione (GSNO) and/or S-nitroso-N-acetyl-cysteine (SNAC) into films and gels based on water soluble polymers, such as poly(vinyl alcohol), poly(vinyl pyrrolidone, or Pluoronic F127 hydrogel, for transdermal NO delivery [19-22]. Their animal results show that repeated topical application of GSNO-containing hydrogel during the early phases of rat cutaneous wound repair accelerates wound closure and re-epithelialization [23]. However, a prolonged NO release would be more desirable from a patient compliance point view in order to avoid repeated applications.

Katsumi and co-workers synthesized a macromolecular carrier for S-nitrosothiol based on bovine scrum albumin (BSA) and poly(ethylene glycol) (PEG)-conjugated BSA by covalently attaching nitrite to cysteine residues on BSA [24, 25]. Similarly, West et al demonstrated in U.S. Pat. No. 7,052,711 that S-nitrosocysteine (CysNO) immobilized within a poly(ethylene glycol) hydrogel reduced platelet adhesion and smooth muscle cell proliferation in in vitro cell culture. However, these reported hydrophilic systems lack the desired stability as the S—NO bond is both thermally and photolytically labile, and susceptible to hemolytic cleavage leading to the spontaneous release of NO and its rapid inactivation. As a result, the nitric oxide release duration from compounds of the prior art cannot be maintained for any extended period, which is, generally, not more than several hours.

Prior art methods of physically mixing GSNO in a polymer [21-24] to form an admixture and mixing a NO precursor with an activator to generate GSNO, either in situ at the time of application as described in WO2006/095193 or in vitro prior to its application to wounds as described in WO2008/031182, do not address the issue of short half-life of GSNO, because once GSNO is formed or released, it is still susceptible to degradation due to heat, moisture and light. In fact, in most of these prior art approaches, the release of NO or GSNO, is usually very rapid and lasts no more than several hours thus necessitates repeated application.

There is, therefore, a need in the art for achieving a stable NO delivery system that provides controllable and durable release of NO for wound healing applications.

PUBLICATIONS

[1] R. M. J. Palmer, A. G. Ferrige, S. Moncada, Nitric oxide release accounts for the biological activity of endothelium-derived relaxing factor, Nature 1987 327 (11): 524-526.

[2] M. B. Witte, A. Barbul, Role of nitric oxide in wound repair, Am. J. Surg. 2002 183 (4): 406-412.

[3] P. H. Groves, A. P. Banning, W. J. Penny, A. C. Newby, The effects of exogenous nitric-oxide on smooth-muscle cell-proliferation following porcine carotid angioplasty, Cardiovasc. Res. 1995 30 (I): 87-96.

[4] D. Y. Wei, E. L. Richardson, K. Y. Zhu, L. W. Wang, X. D. Le, Y. J. He, S. Y. Huang, K. P. Xie, Direct demonstration of negative regulation of tumor growth and metastasis by host-inducible nitric oxide synthase, Cancer Res. 2003 63 (14): 3855-3859.

[5] F. L. M. Ricciardolo, P. J. Sterk, B. Gaston, Nitric oxide in health and disease of the respiratory system, Phys. Rev. 2004 84 (3): 731-765.

[6] N. Toda, T. Okamura, The pharmacology of nitric oxide in the peripheral nervous system of blood vessels, Pharmcol. Rev. 2003 55 (2): 271-324.

[7] A. Ghaffari, C. C. Miller, B. McMullin, A. Ghahary, Potential application of gaseous nitric oxide as a topical antimicrobial agent. Nitric Oxide 2006 14 (1): 21-29.

[8] L. J. Ignarro, Biosynthesis and Metabolism of Endothelium-Derived Nitric Oxide, Annu. Rev. Pharmacol. Toxicol. 1990 (30): 535-560.

[9] L. J. Ignarro, J. M. Fukuto, J. M. Griscavage, N. E. Rogers, R. E. Byrns, Oxidation of nitric oxide in aqueous solution to nitrite but not nitrate: Comparison with enzymatically formed nitric oxide from L-arginine, Proc. Natl. Acad. Sci. USA 1993 (90): 8103-8107.

[10] S. Y. Silva, L. C. Rueda, M. López, I. D. Vélez, C. F. Rueda-Clausen, D. J. Smith, G. Muñoz, H. Mosquera, F. A. Silva, A. Buitrago, H. Díaz, P. López-Jaramillo, Double blind, randomized controlled trial, to evaluate the effectiveness of a controlled nitric oxide releasing patch versus meglumine antimonate in the treatment of cutaneous leishmaniasis. Trials 2006; 7:14-24.

[11] D. J. Smith, D. Chakravarthy, S. Pulfer, M. L. Simmons, J. A. Hrabic, M. L. Citro, J. E. Saavedra, K. M. Davies, T. C. Hutsell, D. L. Mooradian, S. R. Hanson, L. K. Keefer, Nitric Oxide-Releasing Polymers Containing the [N(O)NO]— Group, J. Med. Chem. 1996, 39, 1148-1156.

[12] K. A. Mowery, M. H. Sochoenfisch, J. E. Saavedra, L. K. Keefer, M. E. Meyerhoff, Preparation and characterization of hydrophobic polymeric films that are thromboresistant via nitric oxide release. Biomaterials 2000; 21:9-21.

[13] M. C. Frost, M. M. Reynolds, M. E. Meyerhoff, Polymers incorporating nitric oxide releasing/generating substances to improve biocompatibility of blood-contacting medical devices. Biomaterials 2005; 26:1685-693.

[14] M. M. Batchelor. S. L. Reoma, P. S. Fleser, V. K. Nuthakki, R. E. Callahan, C. J. Shanley, J. K. Politis, J. Elmore, S. I. Merz, M. E. Meyerhoff, More Lipophilic Dialkyldiamine-Based Diazeniumdiolates: Synthesis, Characterization, and Application in Preparing Thromboresistant Nitric Oxide Release Polymeric Coatings, J. Med. Chem. 2003, 46, 5153-5161.

[15] P. G. Parzuchowski, M. C. Frost, M. E. Meyerhoff, Synthesis and Characterization of Polymethacrylate-Based Nitric Oxide Donors, J. Am. Chem. Soc. 2002, 124, 12182-12191.

[16] L. K. Keefer, Progress toward clinical application of the nitric oxide-releasing diazeniumdiolates, Annu. Rev. Pharmacol. Toxicol. 2003 43: 585-607.

[17] N. Hogg, Biological chemistry and clinical potential of S-Nitrosothiols, Free Radical Biology & Medicine, 2000. 28: 1478-1486.

[18] A R Butler, P. Rhodes, Chemistry, analysis, and biological roles of S-nitrosothiols, Anal. Biochem. 1997; 249:1-9.

[19] A. B. Seabra, M. G. de Oliveira, Poly(vinyl alcohol) and blend films for local nitric oxide release. Biomaterials 2004; 25:3773-82.

[20] A. B. Scabra, L. L. da Rocha, M. N. Eberlin, M. G. de Oliveira, Solid films of blended Poly(vinyl alcohol)/poly (vinyl pyrrolidone) for topical S-nitrosoglutathione and nitric oxide release. J. Pharm. Sci. 2005 (94): 994-1003.

[21] S. M. Shishido, A. B. Seabra, W. Loh, M. G. de Oliveira. Thermal and photochemical nitric oxide release from S-nitrosothiols incorporated in Pluronic F127 gel: potential uses for local and controlled nitric oxide release. Biomaterials 2003; 24:3543-53.

[22] A. B. Seabra, A. Fitzpatrick, J. Paul, M. G. de Oliveira, R. Weller. Topically applied S-nitrosothiol-containing hydrogels as experimental and pharmacological nitric oxide donors in human skin. Brit J Dermatol 2004; 151:977-83.

[23] T. P. Amadeu, A. B. Seabra, M. G. de Oliveira, A. M. A. Costa, S-nitrosoglutathione-containing hydrogel accelerates rat cutaneous wound repair, JEADV European Academy of Dermatology and Venereology 2007, 21, 629-637

[24] H. Katsumi, M. Nishikawa, F. Yamashita, M. Hashida, Development of polyethylene glycol-conjugated poly-S-nitrosated serum albumin, a novel S-nitrosothiol for prolonged delivery of nitric oxide in the blood circulation in vivo. J Pharmcol Exp Therap 2005; 314:1117-24.

[25] H. Katsumi, M. Nishikawa, S. F. Ma, F. Yamashita, M. Hashida Physico-chemical, tissue distribution and vasodilation characteristics of nitrosated serum albumin: delivery of nitric oxide in vivo. J Pharm Sci 2004; 93:2343-52.

[26] D A Tomalia, I. Majoros, Dendrimeric supramolecular and supramacromolecular assemblies, J. Macromol. Sci. 2003; C43:411-77.

[27] C. Ladaviere, T. Delair, A. Domard, C. Pichot, B. Mandrand, Covalent immobilization of biological molecules to maleic anhydride and methyl vinyl ether copolymers-A physicochemical approach. J App. Polym Sci 1999; 71: 927-36.

[28] C. Ladavière, C. Lorenzo, A. Elaïssari, B. Mandrand, T. Delair, Electrostatically driven immobilization of peptides onto (maleic anhydride-alt-methyl vinyl ether) copolymers in aqueous media. Bioconjugate Chem 2000; 11:146-52.
[29] L. Allard, V. Cheynet, G. Oriol, B. Mandrand, T. Delair, F. Malle, Versatile Method for production and controlled polymer-immobilization of biologically active recombinant proteins. Biotechnol Bioeng 2002; 80: 341-348.
[30] N. C. Sharma, H. J. Galustians, J. Qaquish, A. Galustians, K. N. Rustogi, M. E. Petrone, P. Chalnis, L. Garcia, A. R. Volpe, H. M. Proskin, The clinical effectiveness of a dentifrice containing triclosan and a copolymer for controlling breath odor measured organoleptically twelve hours after toothbrushing. J Clin Dent 1999; 10:131-4.
[31] K. Yoncheva, E. Lizarraga E, J. M. Irache, Pegylated nanoparticles based on poly(methyl vinyl ether-co-maleic anhydride): preparation and evaluation of their bioadhesive properties. Eur J Pharm Sci 2005; 24:411-9.
[32] N. Dashti, M. Shabani, S. Vardasti, A. Mirsalehian, M. H. Noori Mughehi, A. N. Hatmi, The effect of nitric oxide donor in diabetic wound healing, Iranian J. Publ. Health, 2003 32(4): 59-63.
[33] H. P. Shi, D. Most, D. T. Efron, M. B. Witte, A. Barbul, Supplemental L-arginine enhances wound healing in diabetic rats, Wound Rep. Reg. 2003 11: 198-203
[34] S. Frank, B. Stallmeyer, H. Kampfer, N. Kolb, J. Pfeilschifter, Nitric oxide triggers enhanced induction of vascular endothelial growth factor expression in cultured keratinocytes (HaCaT) and during cutaneous wound repair, FASEB JOURNAL 1999 13 (14): 2002-2014.
[35] K. S. Bohl Masters, S. J. Leibovich, Paula Belem, J. L. West, L. A. Poole-Warren, Effects of nitric oxide releasing poly(vinyl alcohol) hydrogel dressings on dermal wound healing in diabetic mice. Wound Rep. Reg. 2002; 10(5): 286-294.

SUMMARY OF THE INVENTION

Thus, in one aspect, the present invention is directed to a new class of NO delivery systems based on supramacromolecular complexes containing immobilized RSNOs stabilized in a physically cross-linked polymeric network. In which, RSNO precursors covalently attached to a carrier polymer are stabilized via intermolecular complexations with a second polymer, preferably through hydrogen bonding interactions. The resulting supramacromolecular complexes are capable of providing continuous and prolonged NO release with improved storage stability. Here, the term "supramacromolecular" is used to describe molecular assemblies involving precise, 3D-structured, and noncovalently bonded macromolecules [26].

In a further aspect, this invention also provides pharmaceutical compositions comprising the adducts of (1) RSNOs at different NO loading levels; (2) a polymer A bearing anhydride functional groups in the side chains capable of reacting with amine groups on RSNOs; and (3) a polymer B containing proton-accepting groups either in the backbone or in the side chains capable of forming strong hydrogen bonds with polymer A.

In a further aspect the invention also relates to methods of making said NO releasing complexes; and methods of using said complexes.

It further provides a method of making said NO-releasing complexes into a coating through layer-by-layer assemblies via strong intermacromolecular interactions.

In a yet further aspect, this invention provides methods of preparation of such NO-releasing supramacromolecular complexes in a diversity of forms including powders, microparticles, fibers and films. In particularly, this novel nitric oxide releasing polymer complex can be incorporated into dressings and bandages for wound treatment resulting in the release of therapeutic amounts of nitric oxide in a sustained and controlled manner, suitable for treatment of chronic poorly-healed wounds.

This invention also relates to the utilization of a broad-spectrum of GSNO-derived RSNOs as novel NO precursors, which exhibit efficiently NO loading capacity and significantly improved stability.

Further, this invention also provides a method for treating chronic wounds. The present NO-releasing supramacromolecular complexes showed accelerated wound healing in diabetic animal models.

Yet further, this invention presents a new platform for generating therapeutic levels of NO in a controlled and sustained manner, which can be applied directly to local tissues as well as coatings on medical devices.

Most small molecular NO donors are chemical labile in aqueous media. For example, it can be seen from FIG. 1 that NO continuously dissociates from GSNO in acidic and neutral medium under room condition. The present invention provides a useful method to prolong the half-life of RSNOs by attaching them to a macromolecular carrier, thus forming a polymeric NO precursor or prodrug. It has been found unexpectedly that by physically crosslinking the said polymeric NO prodrug through intermolecular hydrogen bonding-interactions with another polymer, the resulting supramacromolecular complexes are capable of providing continuous and prolonged NO generation with further improved RSNO storage stability. Additionally, upon hydration, the present supramacromolecular NO releasing complexes also become bioadhesive thus facilitating the local controlled delivery of NO.

To obtain NO-generating supramacromolecules, it is desirable that all above-mentioned reactions occur very rapidly and all organic solvents involved can be easily removed.

It is an object of the present invention to provide a nitric oxide carrier that provides a simple, stable and biocompatible means for generating a durable release of nitric oxide in the healing of wounds.

It is a further object to provide a method of making said nitric oxide carrier.

It is a further object to provide said nitric oxide carrier in the form of several physical forms, such as a powder, film, fiber, microsphere or coating since solid dosage forms show enhanced stability than aqueous dosage forms during storage and transportation. The present system is superior in many respects to the prior art polymer and gel systems.

The invention provides a bioadhesive supramacromolecular complex comprising the product of a nitric oxide donor covalently linked to a hydrophobic bioadhesive polymeric polyanhydride, which can subsequently form intermolecular hydrogen bonding to a second polymer.

Accordingly, in one aspect the invention provides a bioadhesive supramacromolecular complex of the general formula:

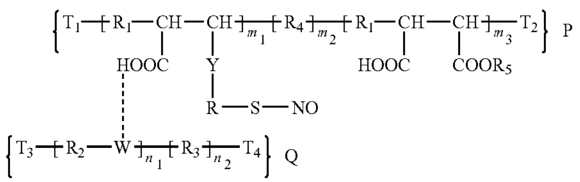

wherein $R_1$ is independently selected from the group consisting of an alkane unsubstituted or substituted with alkoxy groups; $R_2$ is independently selected from the group consisting of C1-6 alkyl; $R_3$ and $R_4$ are independently selected from the group consisting of optionally substituted aliphatic or aromatic alkyl; $R_5$ is independently selected from the group consisting of H or C1-6 alkyl; Regarding structural diversity, all these $R_n$ groups of Formula can be varied over a wide range to produce isolable materials; W is a hydrogen bond-accepting functional group-containing entity; Y is a carboxylic acid ester or amide linkage; R is independently selected peptide linking group; $T_1$, $T_2$, $T_3$ and $T_4$ are independently selected polymer residues; and $m_1$, $m_2$, $m_3$, $n_1$ and $n_2$ are integers selected from at least 25; and wherein P has a molecular weight of about $1\times10^3$ to $1\times10^7$ and Q has a molecular weight of about $1\times10^3$ to $1\times10^7$.

In a further aspect the invention provides a bio-adhesive supramacromolecular complex of the general formula:

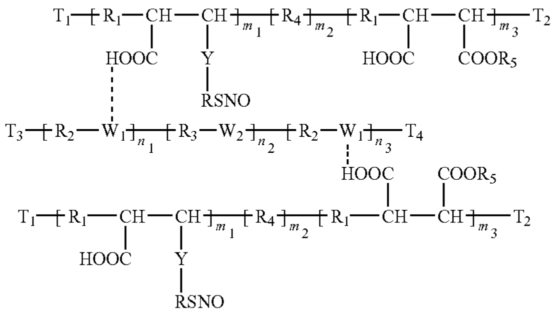

wherein $R_1$ is an alkyl vinyl ether ($C_1$-$C_5$), ethylene, propylene, isobutylene, butadiene, 1-octadecene, styrene, maleic acid, or maleic anhydride unit; $W_1$ and $W_2$ are hydrogen-bond accepting functional group-containing entities selected from vinylpyrrolidone, ethylene oxide or propylene oxide, vinyl acetate, alkoxyl substituted glucopyranose, glucosamine, and acetylglucosamine; $R_2$ and $R_3$ are independently selected from unsubstituted alkyl or optionally substituted aliphatic or aromatic alkyl; Y is a carboxylic acid ester or amide linkage; $R_4$ is a substituted aliphatic or aromatic alkyl; $R_5$ is independently selected from the group consisting of H or C1-6 alkyl; RSNO is a primary amine containing S-nitrosothiol of cysteine, γ-Glu-Cys, α-Glu-Cys, glutathione, homoglutathione, glutathione ethyl ester, hydroxymethyl-glutathione, γ-Glu-Cys-Glu, α-Glu-Cys-Gly, α-Glu-Cys-β-Ala, α-Glu-Cys-Ser, α-Glu-Cys-Glu, other glutathione analog containing —SH and —$NH_2$ and/or —OH functional groups, or one of the following peptides: $(\gamma\text{-Glu-Cys})_q$, $(\gamma\text{-Glu-Cys})_q$-Gly, $(\gamma\text{-Glu-Cys})_q$-β-Ala, $(\gamma\text{-Glu-Cys})_q$-Ser, $(\gamma\text{-Glu-Cys})_q$-Glu, $(\alpha\text{-Glu-Cys})_q$, $(\alpha\text{-Glu-Cys})_q$-Gly, $(\alpha\text{-Glu-Cys})_q$-β-Ala, $(\alpha\text{-Glu-Cys})_q$-Ser, and $(\alpha\text{-Glu-Cys})_q$-Glu, where q=2-11; $T_1$, $T_2$, $T_3$ and $T_4$ are independently selected polymer residues; $m_1$, $m_2$, $m_3$, $n_1$, $n_2$, and $n_3$ are integers greater than 25.

The supramacromolecular complex is, preferably, wherein $T_1$-[—$R_1$—CH(COOH)—CH(Y—RSNO)-$]_{m1}$-[—$R_4$-$]_{m2}$-[—$R_1$—CH(COOOC)CH-$]_{m3}$-$T_2$ is a reaction adduct of RSNO and a maleic anhydride polymer or copolymer, wherein the maleic anhydride polymer or copolymer is selected from the group consisting of poly(methyl vinyl ether-alt-maleic anhydride), poly(maleic acid-co-maleic anhydride), poly(maleic anhydride), poly(vinylpyrrolidone-co-dimethyl maleic anhydride), poly(vinylacetate-co-maleic anhydride), poly(ethylene-alt-maleic anhydride), polyisobutylene-alt-maleic anhydride), polystyrene-alt-maleic anhydride), poly(ethylene-co-ethyl acrylate-co-maleic anhydride), and poly(maleic anhydride-alt-1-octadecene).

The supramacromolecular complex is, preferably, wherein $R_1$ is a maleic acid copolymer, and more preferably, wherein the maleic acid copolymer is selected from the group consisting of poly(methyl vinyl ether-co-maleic acid) poly(vinylpyrrolidone-co-dimethyl maleic acid), poly(ethylene-co-maleic acid), poly(isobutylene-co-maleic acid), poly(styrene-co-maleic acid), poly(ethylene-co-ethyl acrylate-co-maleic acid), poly(maleic acid-co-octadecene), polyethylene-graft-maleic acid, polypropylene-graft-maleic acid, and polyisoprene-graft-maleic acid.

In a further aspect the invention provides a bio-adhesive supramacromolecular complex of the general formula:

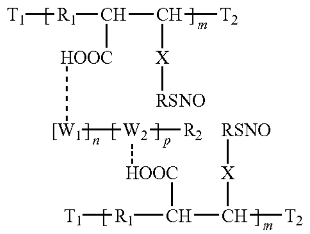

wherein $R_1$ is an alkyl vinyl ether ($C_1$-$C_5$), ethylene, propylene, isobutylene, butadiene, 1-octadecene, styrene, maleic acid, or maleic anhydride unit; $W_1$ and $W_2$ are hydrogen-bond accepting functional group-containing entities selected from vinylpyrrolidone, ethylene oxide or propylene oxide, vinyl acetate, alkoxyl substituted glucopyranose, glucosamine, and acetylglucosamine; $R_2$ is H, a fatty acid ester, or fatty alcohol; X is a carboxylic acid ester or amide linkage; RSNO is a S-nitrosothiol of cysteine, γ-Glu-Cys, α-Glu-Cys, glutathione, homoglutathione, glutathione ethyl ester, hydroxymethyl-glutathione, γ-Glu-Cys-Glu, α-Glu-Cys-Gly, α-Glu-Cys-β-Ala, α-Glu-Cys-Ser, α-Glu-Cys-Glu, other glutathione analog containing —SH and —$NH_2$ and/or —OH functional groups, or one of the following peptides: $(\gamma\text{-Glu-Cys})_q$, $(\gamma\text{-Glu-Cys})_q$-Gly, $(\gamma\text{-Glu-Cys})_q$-β-Ala, $(\gamma\text{-Glu-Cys})_q$-Ser, $(\gamma\text{-Glu-Cys})_q$-Glu, $(\alpha\text{-Glu-Cys})_q$, $(\alpha\text{-Glu-Cys})_q$-Gly, $(\alpha\text{-Glu-Cys})_q$-β-Ala, $(\alpha\text{-Glu-Cys})_q$-Ser, and $(\alpha\text{-Glu-Cys})_q$-Glu, where q=2-11; $T_1$ and $T_2$ are terminal groups; m, n and p are integers greater than 25.

The supramacromolecular complex is, preferably, wherein $T_1$-[—$R_1$—CH(COOH)—CH(X—RSNO)-$]_m$-$T_2$ is a reaction adduct of RSNO and a maleic anhydride polymer or copolymer, wherein the maleic anhydride polymer or copolymer is selected from the group consisting of poly(methyl vinyl ether-alt-maleic anhydride), poly(maleic acid-co-maleic anhydride), poly(maleic anhydride), poly(vinylpyrrolidone-co-dimethyl maleic anhydride), poly(vinylacetate-co-maleic anhydride), polyethylene-alt-maleic anhydride), poly (isobutylene-alt-maleic anhydride), poly(styrene-alt-maleic anhydride), poly(ethylene-co-ethyl acrylate-co-maleic anhydride), and poly(maleic anhydride-alt-1-octadecene).

In the present invention, maleic anhydride containing polymers are employed to immobilize RSNOs, preferably GSNO, through an acetylation reaction between pendant anhydride groups and the primary amino group in GSNO. The reactivity of maleic anhydride containing polymers under generally mild conditions has made them particularly suited for the immobilization of bioactive agents [27-29]. For example in US2001/0046476, bactericide, flavorant and essential oil have been covalently bonded to poly(methyl vinyl ether-alt-maleic anhydride) (PVMMA) and its derivatives to provide slow-release oral care compositions.

To achieve effective local delivery of NO, it would be very advantageous to employ PVMMA as the NO carrier in view of its outstanding bioadhesive properties which effectively lengthens the residence time of the present NO-releasing supramacromolecular complexes at the wound site. The hydrophobic nature of PVMMA and its surface erosion characteristics will facilitate the achievement of an extended NO release. Indeed, PVMMA and its modified derivatives have found many applications in dental adhesives, cosmetics and drug delivery systems [30-31, U.S. Pat. No. 6,355,706, US 2007/196459, WO 2006/015093, WO 2001/087276].

The nitric oxide donor RSNO is, preferably, selected from the group consisting of S-nitrosothiols of cysteine, γ-Glu-Cys, α-Glu-Cys, glutathione (GSH), glutathione ethyl ester, homoglutathione, hydroxymethyl-glutathione, γ-Glu-Cys-Glu, α-Glu-Cys-Gly, α-Glu-Cys-β-Ala, α-Glu-Cys-Ser, α-Glu-Cys-Glu, other glutathione analog containing —SH and —$NH_2$ and/or —OH functional groups, or one of the following peptides: $(\gamma\text{-Glu-Cys})_n$, $(\gamma\text{-Glu-Cys})_n$-Gly (also known as phytochelatins), $(\gamma\text{-Glu-Cys})_n$-β-Ala, $(\gamma\text{-Glu-Cys})_n$-Ser, $(\gamma\text{-Glu-Cys})_n$-Glu, $(\alpha\text{-Glu-Cys})_n$, $(\alpha\text{-Glu-Cys})_n$-Gly, $(\alpha\text{-Glu-Cys})_n$-β-Ala, $(\alpha\text{-Glu-Cys})_n$-Ser, and $(\alpha\text{-Glu-Cys})_n$-Glu, where n=2-11.

The $T_3$-[—$R_2$—W-$]_{n1}$-[—$R_3$—$]_{n2}$-$T_4$ and the $T_3$-[—$R_2$—$W_1$-$]_{n1}$-[—$R_3$—$W_2$-$]_{n2}$-[—$R_2$—$W_1$-$]_{n3}$-$T_4$ hydrogen bond accepting polymer is, preferably, selected from the group consisting of poly(vinyl pyrrolidone), polyethylene glycol, poly(ethylene oxide), poly(vinyl pyrrolidone-co-vinyl acetate), polyethylene oxide-polypropylene oxide block copolymers (Pluronics or Polaxomers), polyethylene glycol fatty alcohol esters, polyethylene glycol fatty acids esters, ethyl cellulose, and chitosan, and more preferably, poly(vinyl pyrrolidone).

Preferably, Y.R.SNO is an amido-5-nitrosoglutathione or amido-phytochelatin.

in a further aspect, the invention provides a method of making a bio-adhesive, supramacromolecular nitric oxide generatable polymer complex, said method comprising i. covalently linking a S-nitroso compound having an amino linking group with a bio-adhesive, hydrophobic polyanhydride compound to form a nitric oxide donor polymeric carrier, and
ii. mixing said carrier with an hydrophilic intermolecular hydrogen bond-acceptable polymer to produce said supramacromolecular nitric oxide generatable complex.

Preferred nitric oxide donor RSNO is selected from the group consisting of S-nitrosothiols of cysteine, γ-Glu-Cys, α-Glu-Cys, glutathione (GSH), homoglutathione, hydroxymethyl-glutathione, γ-Glu-Cys-Glu, α-Glu-Cys-Gly, α-Glu-Cys-β-Ala, α-Glu-Cys-Ser, α-Glu-Cys-Glu, other glutathione analogs containing —SH and —$NH_2$ and/or —OH functional groups, or one of the following peptides: $(\gamma\text{-Glu-Cys})_n$, $(\gamma\text{-Glu-Cys})_n$-Gly (also known as phytochelatins), $(\gamma\text{-Glu-Cys})_n$-β-Ala, $(\gamma\text{-Glu-Cys})_n$-Ser, $(\gamma\text{-Glu-Cys})_n$-Glu, $(\alpha\text{-Glu-Cys})_n$, $(\alpha\text{-Glu-Cys})_n$-Gly, $(\alpha\text{-Glu-Cys})_n$-β-Ala, $(\alpha\text{-Glu-Cys})_n$-Ser, and $(\alpha\text{-Glu-Cys})_n$-Glu, where n=2-11. Most preferably, the S-nitrosothiol compound is GSNO or a phytochelatin.

Preferred polyanhydride compounds are maleic anhydride polymer or copolymers with molecular weight (Mw) ranging from about 5,000 to 2,000,000, wherein the maleic anhydride polymer or copolymer, for example, is preferably selected from the group consisting of poly(methyl vinyl ether-alt-maleic anhydride), poly(maleic acid-co-maleic anhydride), poly(maleic anhydride), poly(vinylpyrrolidone-co-dimethyl maleic anhydride), poly(vinylacetate-co-maleic anhydride), poly(ethylene-alt-maleic anhydride), poly(isobutylene-alt-maleic anhydride), poly(styrene-alt-maleic anhydride), poly (ethylene-co-ethyl acrylate-co-maleic anhydride), and poly (maleic anhydride-alt-1-octadecene). Most preferably, the polyanhydride compound is poly(methyl vinyl ether-alt-maleic anhydride).

The hydrogen bond accepting polymer is, preferably, selected from the group, with molecular weight (Mw) from about 5,000 to 7,000,000, consisting of poly(vinyl pyrrolidone), polyethylene glycol, poly(ethylene oxide), poly(vinyl pyrrolidone-co-vinyl acetate), polyethylene oxide-polypropylene oxide block copolymers (Pluronics or Polaxomers), polyethylene glycol fatty alcohol esters, polyethylene glycol fatty acids esters, ethyl cellulose, and chitosan, most preferably a method as claimed in claim 17 wherein said hydrogen bond acceptable polymer is poly(vinyl pyrrolidone).

The resulting supramacromolecular nitric oxide generatable polymer complex preferably contains a polyanhydride compound and a hydrogen bond accepting polymer in relative weight proportions ranging from 1:9 to 9:1, more preferably, 2:5 to 5:2, and most preferably 1:2 to 2:1.

The total loading of the nitric oxide donor RSNOs in the resulting supramacromolecular nitric oxide generatable polymer complex is preferably in the range of 1 to 50 wt %, more preferably 1 to 30%, and most preferably 5 to 20%.

The invention, in a further aspect, provides a bio-adhesive, supramacromolecular nitric oxide generatable complex when made by a method as hereinabove defined.

In a yet further aspect, the invention provides a pharmaceutical composition comprising an effective wound healing amount of said supramacromolecular complex, as hereinabove defined, and a physiological acceptable carrier.

In a yet further aspect, the invention provides a layer-by-layer assembly method for fabricating the said supramacromolecular complex, as hereinabove defined, into coatings.

In a yet further aspect, the invention provides an electrospinning method for producing the said supramacromolecular complex, as hereinabove defined, as spun fibers.

In a yet further aspect, the invention provides a ultrasonic spraying method for producing the said supramacromolecular complex, as hereinabove defined, as microspheres.

Thereby, the invention provides a supramacromolecular complex, as hereinabove defined, in the physical form of a powder, microcapsule, spun fiber, or coating on a surface of a substrate, for example, a catheter or stent.

Thus, the present invention is directed to a novel nitric oxide-releasing polymer complex, which, in powder form, can serve as wound dressing and be incorporated into transdermal patches, bandages, sutures, and the like. It can also take the form of a coating by applying the polymer complex, prior to solidifying via layer-by-layer method, to blood contacting surfaces on a medical device. This supramacromolecular complex produces a therapeutic amount of nitric oxide in a sustained and controlled manner and delivers it to the diseased tissues, such as those in chronic, poorly-healed wounds.

Thus, in a further aspect, the present invention is directed to the employment of electrospinning apparatus to produce non-woven mats during the loading procedure or coated substrate during the spinning process, based on supramacromolecular complexes as hereinabove defined. The resultant mats can be directly applied locally to the wound area.

Thus, in a further aspect, the present invention is directed to the utilization of ultrasonic atomization technology to produce evenly sized microspheres based on supramacromolecular complexes as hereinabove defined. The resultant microspheres can be further incorporated into capsules or coated on a substrate during the spraying process.

Thus, in a further aspect, the invention provides a skin covering for application to the skin, the covering incorporating an effective wound healing amount of a supramacromolecular complex, as hereinabove defined. The skin covering may be a bandage or wound dressing.

In a further aspect, the invention provides a method of enhancing the healing of a skin wound or infection, said method comprising applying an effective wound or infection healing amount of a bio-adhesive supramacromolecular complex or pharmaceutically acceptable composition thereof, as hereinabove defined, to said wound.

In a yet further aspect, the invention provides use of a bio-adhesive supramacromolecular complex or pharmaceutically acceptable composition thereof, as hereinabove defined, for enhancing the healing of a skin wound or infection.

Thus, the present invention comprises three essential key elements, namely, (1) a polymeric carrier which is hydrophobic, biocompatible, bioerodible and contains anhydride functional groups, for example, such as poly(methyl vinyl ether-alt-maleic anhydride) [PVMMA], (2) a nitric oxide donor such as S-nitrosoglutathione (GSNO) or other S-nitrosated glutathione derivatives that can be covalently attached under mild conditions to the anhydride groups on the macromolecular backbone or side chain of the above polymeric carrier, and (3) a second polymer, for example, such as polyvinyl pyrrolidone) [PVP], which forms strong physical intermolecular complexes with the first polymeric carrier.

Thus, the field of the invention relates to devices and methods for treating wounds and infections, and more specifically, the treatment of wounds and infections with prolonged local release of nitric oxide. The complexes of the present invention can be made into powders and incorporated in the bandage or wound dressing to facilitate wound healing. Additionally, it can be deployed as an ingredient of inhalation formulation to decrease pulmonary hypertension or applied to the treatment of circulation disorders.

Prolonged nitric oxide release from the bio-adhesive supramacromolecular complex over a period of at least about seven days provides efficacious treatment of wounds and infections. Without being bound by theory, we believe that the efficacy is due to the presence of the hydrogen bond-accepting functional group e.g. PVP, being hydrogen bonded through the carboxylic acid group of the bio-adhesive hydrophobic polymer, e.g. PVMMA, which slows down the rate of formation of disulfide bonds and release of nitric oxide from sterically hindered RSNOs embedded in the PVMMA hydrophobic matrix.

BRIEF DESCRIPTION OF THE DRAWINGS

The following drawings form part of the present specification and are included to further demonstrate the essential aspects of the present invention, In order that the invention may be better understood, certain preferred embodiments will be illustrated by way of example only with reference to the drawings, wherein.

DETAILED DESCRIPTION OF PREFERRED EMBODIMENTS

EXAMPLES

Figure 1:
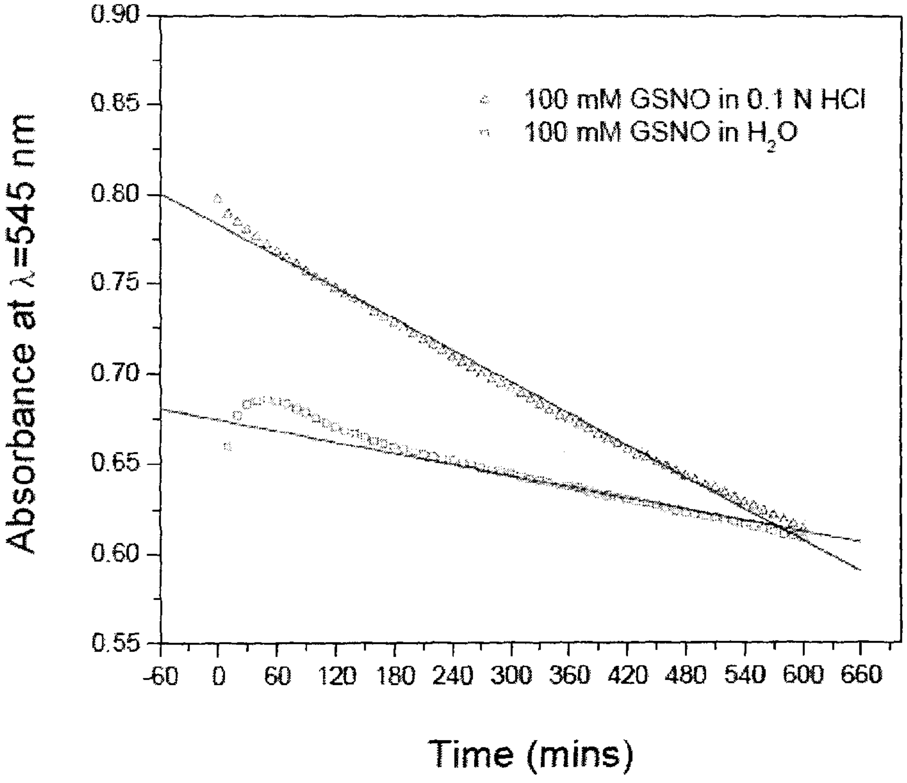
FIG. 1 shows the time course of NO decomposition kinetics from GSNO in acidic and neutral medium at 22° C.

The invention will be more readily understood by reference to the following examples, which are included merely for purpose of further illustration of certain aspects and the embodiment of the present invention and are not intended to limit the invention in any way.

Preparation of RSNOs-PVMMA/PVP Complex Powder

Materials

In the following experiments, Reduced glutathione (GSH), Reduced glutathione ethyl ester (GSHEE), sodium nitrite ($NaNO_2$), sulfanilamide (SULF) and N-(1-naphthyl)ethylenediamine dihydrochloride) (NEDD) were obtained from Sigma-Aldrich Chemical Co. (Oakville, Calif.). All phytochelatins were purchased from AnaSpec Inc. (San Jose, Calif., US).

All polymers were obtained from ISP (New Jersey, USA) and Dow Chemical Company (Midland, Mich.). Other chemicals and solvents of analytical reagent grade were obtained from Sigma Aldrich, and they were used as received unless stated otherwise. A Milli-Q grade (Millipore, SA, France) deionized water was used for all solutions and buffers.

All PVMMA and PVP used in the following examples are PVMMA AN-169 and PVP K-90, unless stated otherwise.

Example 1

Synthesis of RSNOs

Synthesis of RSNOs is accomplished via nitrosation of thiols according to the following reaction equation, $$RSH + (HNO)_2 \xrightarrow{H_3O^+} RSNO + H_2O \qquad \text{Equation (1)}$$

The reaction is very rapid, effective, and quantitative at least from the synthetic viewpoint. However, this reaction often generates unstable product in its pure state. The homolysis of RSNO giving rise to disulfide bridge formation, as described in the reaction equation below, is the main mechanism responsible for its thermal instability.

$$RSNO + RSNO \xrightarrow{metal, heat\ \&\ light} RS-SR + 2NO \qquad \text{Equation (2)}$$

Detailed information about this reaction will be described in the following examples.

A. Experimental Procedure for Preparing GSNO

GSNO was readily prepared by reacting reduced glutathione (GSH) and equimolar nitrites in acidic medium protected from exposure to light.

Scheme 1

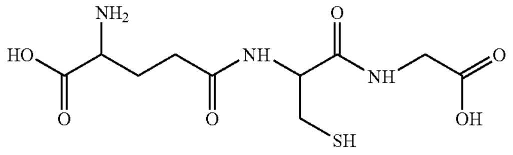

GSH ($C_{10}H_{17}N_3O_6S$ Mw: 307.33)

Briefly, to a stirred ice-cold solution of glutathione (GSH) (154 mg, 0.5 mmol) in 5 ml of 0.2 N HCl was added a portion of $NaNO_2$ (35 mg, 0.5 mmol). This reaction gives GSNO in a high yield of more than 80%. The final red solution was protected from light with aluminum foil and stable in the dark, which allow it to be used directly after synthesis without purification.

B. S-Nitroso Reaction of GSHEE

The S-nitrosation of glutathione ethyl ester (GSHEE) (Scheme 2) was achieved in a similar fashion. Briefly, to a stirred ice-cold solution of GSHEE (67 mg, 0.2 mmol) in 2 ml of 0.2 N HCl was added a portion of $NaNO_2$ (14 mg, 0.2 mmol). The resultant red solution was stored in a vial protected from light with aluminum foil.

Scheme 2

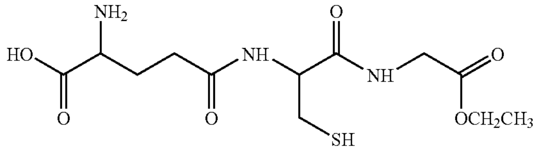

GSHEE ($C_{12}H_{21}N_3O_6S$) Mw: 335.4

C. S-Nitroso Reaction of Phytochelatin 5

The S-nitrosation of phytochelatins 5 (PC5) (Scheme 3) was achieved in a similar fashion. Except that the molar ratio of PC5 to $NaNO_2$ was 1:5 taking into account the 5 thiols group in each PC5 molecule.

Scheme 3

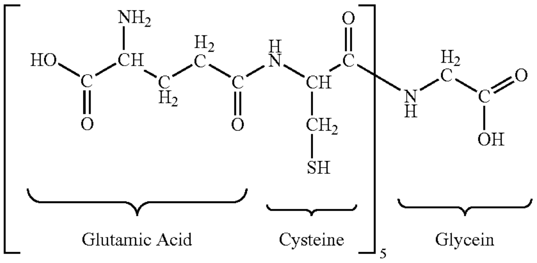

Phytochelatin, PC5 Mw: 1237.4

In brief, 3 mg PC5 (3.2325 μmol) was firstly dissolved in 100 μl of 0.2 N HCl in the ice bath, then to this solution was immediately added 100 μl of fresh prepared $NaNO_2$ solution (11.152 mg/ml). The resultant pink solution was stored in a vial protected from light with aluminum foil.

D. S-Nitroso Reaction of Homo-Phytochelatin2

The S-nitrosation of homo-phytochelatins2 (homo-PC2) (Scheme 4) was achieved in a similar fashion. Except that the molar ratio of homo-PC2 to $NaNO_2$ is 1:2 taking into account the 2 thiol groups in each homo-PC2 molecule.

Scheme 4

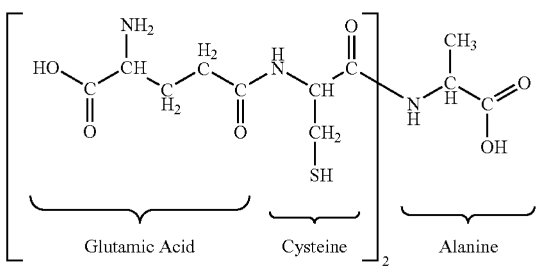

Homo-Phytochelatin2, Homo-PC2 Mw: 554.6

In brief, 1 mg homo-PC2 (1.8031 μmol) was firstly dissolved in 50 μl of 0.2 N HCl in the ice bath, then to this solution was immediately added 50 μl of fresh prepared $NaNO_2$ solution (2.4883 mg/ml). The resultant pink solution was stored in a vial protected from light with aluminum foil.

Example 2

Conjugation of RSNOs to PVMMA

A notable character of maleic anhydride copolymer is the well-known high reactivity of the anhydride moieties with primary amine groups, and to lower degrees, with alcohols. This reaction can be performed either in the dissolved state of the copolymers or via surface chemistry following interfacial presentation of some bioactive molecules. Such acylation reaction can take place under generally mild conditions, which, in the present case, was accomplished spontaneously at room temperature within 20 min.

In principle, all RSNOs containing primary amine group are capable of reacting with maleic anhydride copolymers such as PVMMA according to Scheme 5. Such reaction also resulted in the formation of free carboxylic acid group, which are essential in providing protons for the subsequent essential step of forming intermacromolecular complexes with a second polymer. It is very important that RSNO should be prepared first before conjugation with PVMMA because the thiol group is more reactive than the amine group with respect to reacting with the anhydride group.

Scheme 5

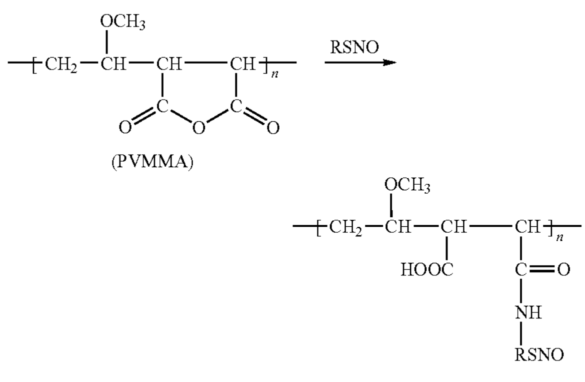

A. Conjugation of GSNO to PVMMA

The facile attachment of GSNO to PVMMA was achieved via a heterogeneous reaction of GSNO and PVMMA, since GSNO has to be dissolved in 0.1 N HCl and PVMMA in acetone separately, and the fact that acetone and aqueous HCL happen to be precipitating agents for GSNO and PVMMA, respectively. Therefore, the grafting reaction takes place at the interface of GSNO and PVMMA in solution. The GSNO loading in the following examples can be achieved up to 50% relative to the PVMMA weight.

A1. Conjugation of GSNO to PVMMA with 7.52% Loading

Firstly, 500 mg PVMMA was homogeneously dissolved in 10 ml acetone. 1 ml of GSNO solution obtained in accordance with Example 1A was then added dropwise into the PVMMA solution under stirring in an ice bath. Subsequently, the solution was poured into a Teflon dish and placed into a fume hood; acetone was removed by either air-drying or vacuum drying under room temperature and protected from light exposure. The obtained GSNO-PVMMA, in the form of a pink powder, was collected and stored in desiccator. Additionally, a portion of the resultant solution was kept without drying for the next reaction step.

A2. Conjugation of GSNO to PVMMA with 15.04% Loading

Firstly, 500 mg PVMMA was homogeneously dissolved in 10 ml acetone. 2 ml of obtained GSNO solution in accordance with Example 1A was then added dropwise into the PVMMA solution under stirring in an ice bath. Subsequently, the solution was poured into a Teflon dish and placed into a fume hood, acetone was removed by either air-drying or vacuum drying under room temperature and protected from the light exposure. The obtained GSNO-PVMMA, in the form of pink powder was collected and stored in desiccator. Additionally, a portion of the resultant solution was kept without drying for the next reaction step.

A3. Conjugation of GSNO to PVMMA with 30% Loading

Firstly, 500 mg PVMMA was homogeneously dissolved in 10 ml acetone. 4 ml of obtained GSNO solution in accordance with Example 1A was then added dropwise into the PVMMA solution under stirring in an ice bath. Subsequently, the solution was poured into a Teflon dish and placed into a fume hood, acetone was removed by either air-drying or vacuum drying under room temperature and protected from the light exposure. The obtained GSNO-PVMMA in the form of pink powder was collected and stored in desiccator. Similarly, a portion of the resultant solution was kept without drying for the next reaction step.

B. Conjugation of S-Nitroso-GSHEE to PVMMA

The attachment of S-Nitroso-GSHEE to PVMMA with 8.1 wt % loading was achieved by the same method described above. Briefly, 1 ml S-Nitroso-GSHEE (according to Example 1B) was added dropwise to 10 ml of 5% PVMMA acetone solution under stirring in an ice bath. The mixture was allowed to react for 10 min, then poured into a Teflon dish and air dried in the dark. Due to the rapid volatilization of acetone, the resultant pink powder was collected in 1 hour and subsequently stored in a desiccator. Likewise, a portion of the resultant solution was kept without drying for the next reaction step.

C. Conjugation of S-Nitroso-PC5 to PVMMA

The attachment of S-Nitroso-PC5 to PVMMA with 6 wt % loading was achieved by the same method described above. Briefly, 50 mg of PVMMA was firstly dissolved in 5 ml acetone, then 200 μl S-Nitroso-PC5 solution (according to Example 1C) was added dropwise to PVMMA solution under stirring in an ice bath, the mixture was allowed to react for 10 min, then used immediately for next step after the synthesis.

D. Conjugation of S-Nitroso-Homo-PC2 to PVMMA

The attachment of S-Nitroso-PC5 to PVMMA was achieved by the same method described above. 20 mg PVMMA was firstly dissolved in 2 ml acetone, then 100 μl S-Nitroso-PC5 solution (according to Example 1D) was added dropwise to PVMMA solution under stirring in an ice bath, the mixture was allowed to react for 10 min, then used immediately for next step after the synthesis.

Example 3

Complexation of RSNOs Conjugated PVMMA with PVP

The complexation of RSNOs-PVMMA and PVP is based on the interpolymeric hydrogen bonding interaction shown in Scheme 6.

Scheme 6

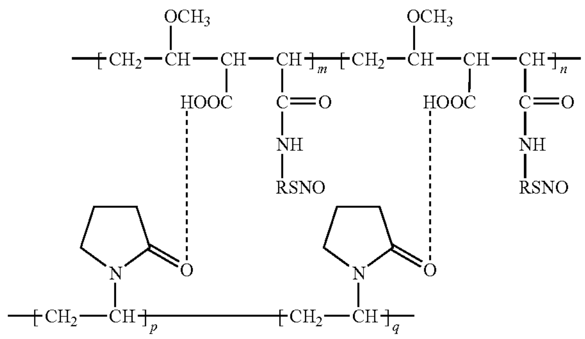

A. Preparation of GSNO-PVMMA/PVP Complex

To prepare the GSNO-PVMMA/PVP complex, a 6.36 wt % PVP solution was first prepared in a mixture of 10:1 (volume ratio) acetone and ethanol. Since PVP can not be dissolved in pure acetone, a certain amount of ethanol has to be added to facilitate the solution preparation in accordance with the composition of the corresponding GSNO-PVMMA solution.

A1 Preparation of GSNO-PVMMA/PVP Complex with 7.52% GSNO Loading Relative to PVMMA 3 ml ethanol was firstly added to a GSNO-PVMMA solution (10/1 acetone/0.1 N HCl according to Example 2A1) prior to the complex formation. Subsequently, a measured amount of PVP solution was quickly poured into the GSNO-PVMMA solution under vigorous stirring in an ice bath. As the complex formation took place through intermolecular hydrogen bonding, the viscosity of the resultant mixture showed a distinctive increase giving rise to a pink gel-like product with the gelation degree varying with composition; PVMMA/PVP weight ratios were adjusted from 1:9 to 9:1 via introducing different volume of PVP solution.

A2 Preparation of GSNO-PVMMA/PVP Complex with 15.04% GSNO Relative to PVMMA 4 ml ethanol was firstly added into GSNO-PVMMA solution (10/2 acetone/0.1 N HCl according to Example 2A2) prior to the complex formation. Subsequently, a measured amount of PVP solution was quickly poured into the GSNO-PVMMA solution under vigorous stirring in an ice bath. As the complex formation took place, through intermolecular hydrogen bonding, the viscosity of the resultant mixture showed a distinctive increase giving rise to a pink gel-like product with the gelation degree varying with composition; PVMMA/PVP weight ratio were adjusted from 1:9 to 9:1 via introducing different volume of PVP solution.

A3 Preparation of GSNO-PVMMA/PVP Complex with 30% GSNO Relative to PVMMA 5 ml ethanol was firstly added into GSNO-PVMMA solution (10/4 acetone/0.1 N HCl according to Example 2A2) prior to the complex formation. Subsequently, a measured amount of PVP solution was quickly poured into the GSNO-PVMMA solution under vigorous stirring in the ice bath. As the complex formation took place, through intermolecular hydrogen bonding, the viscosity of the resultant mixture showed a distinctive increase, giving rise to a pink gel-like product with the gelation degree varying with composition; PVMMA/PVP weight ratio was adjusted from 1:9 to 9:1 via introducing different volume of PVP solution.

Afterwards, all of the resulting semi-solid products from A1, A2, and A3 of Example 3 were transferred into a Teflon dish and air dried in the fume hood. After the pink polymer complex completely solidified, the brittle product so obtained was mixed with dry ice and milled into powder in a Micro-Mill™ laboratory grinding mill. Different size fractions of the final pink powder were separated on a Mini-Sieve Micro Sieve Set and stored in amber containers prior to use.

B. Preparation of S-Nitroso-GSHEE-PVMMA/PVP Complex

To prepare the S-Nitroso-GSHEE-PVMMA/PVP Complex, a 6.36 wt % PVP solution was first prepared in a mixture of 10:1 (volume ratio) acetone and ethanol. Since PVP can not be dissolved in acetone, 1 ml ethanol was added to (10/1 acetone/0.1 N HCl) of S-Nitroso-GSHEE-PVMMA solution (according to Example 2B) prior to the complex formation. Subsequently, a measured amount of PVP solution was quickly poured into the S-Nitroso-GSHEE-PVMMA solution under vigorous stirring in an ice bath, immediately giving risk to a pink gel-like complex; PVMMA/PVP weight ratio was adjusted from 9:1 to 1:9 via different volume of PVP solution. The resulting complex was air dried, mixed with dry ice and milled into powder in a Micro-Mill™ laboratory grinding mill. Different size fractions of the final pink powder were separated on a Mini-Sieve Micro Sieve Set and stored in amber containers prior to use.

C. Preparation of S-Nitroso-PC5-PVMMA/PVP Complex

To make the S-Nitroso-PC5-PVMMA/PVP Complex, a 6.36 wt % PVP solution was first prepared in a mixture of 10:1 (volume ratio) acetone and ethanol. 0.5 ml ethanol was added to 5 ml S-Nitroso-PC5-PVMMA solution (according to Example 2C) prior to the complex formation. Subsequently, a measured amount of PVP solution was quickly poured into the S-Nitroso-PC5-PVMMA solution, immediately giving rise to the pink gel-like complex. PVMMA/PVP weight ratio was adjusted from 9:1 to 1:9 via different volume of PVP solution. The resulting complex was air dried, mixed with dry ice and milled into powder in a Micro-Mill™ laboratory grinding mill. Different size fractions of the final pink powder were separated on a Mini-Sieve Micro Sieve Set and stored in amber containers prior to use.

D. Preparation of S-Nitroso-HomoPC2-PVMMA/PVP Complex

To make the S-Nitroso-HomoPC2-PVMMA/PVP Complex, a 6.36 wt % PVP solution was first prepared in a mixture of 10:1 (volume ratio) acetone and ethanol. 0.2 ml ethanol was added into 2 ml S-Nitroso-HomoPC2-PVMMA solution (according to Example 2D) prior to the complex formation. Subsequently, a measured amount of PVP solution was quickly poured into S-Nitroso-HomoPC2-PVMMA solution, immediately giving rise to the pink gel-like complex. PVMMA/PVP weight ratio was adjusted from 9:1 to 1:9 via different volume of PVP solution. The resulting complex was air dried, mixed with dry ice and milled into powder in a Micro-Mill™ laboratory grinding mill. Different size fractions of the final pink powder were separated on a Mini-Sieve Micro Sieve Set and stored in amber containers prior to use.

Example 4

Characterization of RSNOs-PVMMA/PVP Complex Powder

UV-Vis Spectra

Figure 2:
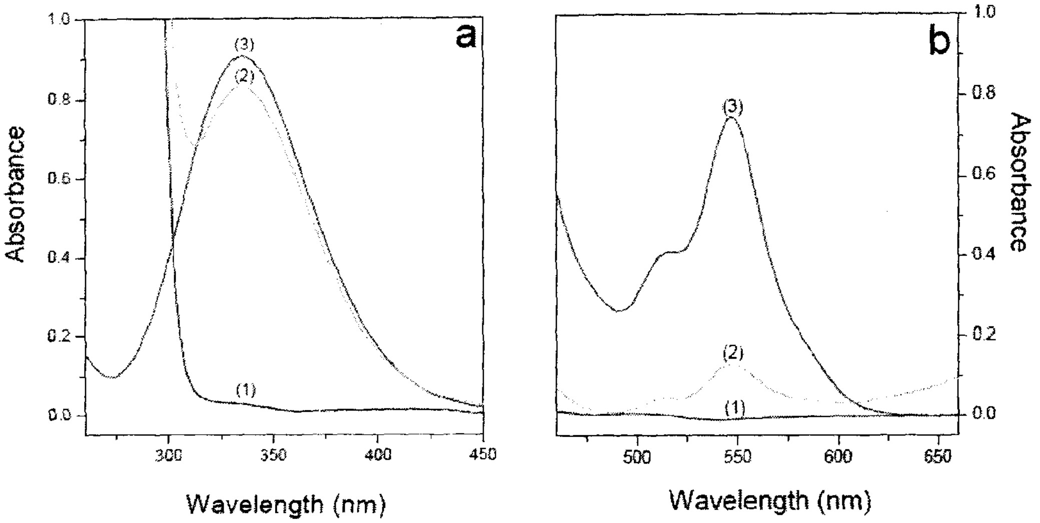
FIG. 2 shows the UV-Vis spectra of GSNO, GSNO-PVMMA, the maximum absorption in UV (a) and visible range (b), which corresponds to the characteristic absorbance of S—NO bond at λ=336 nm and λ=545 nm, can be assigned to σ→σ□ and π→π□ electronic transition, respectively. (1) pure PVMMA dissolved in acetone; (2) GSNO in aqueous medium; (3) GSNO-conjugated PVMMA in the aqueous medium.
Figure 3:
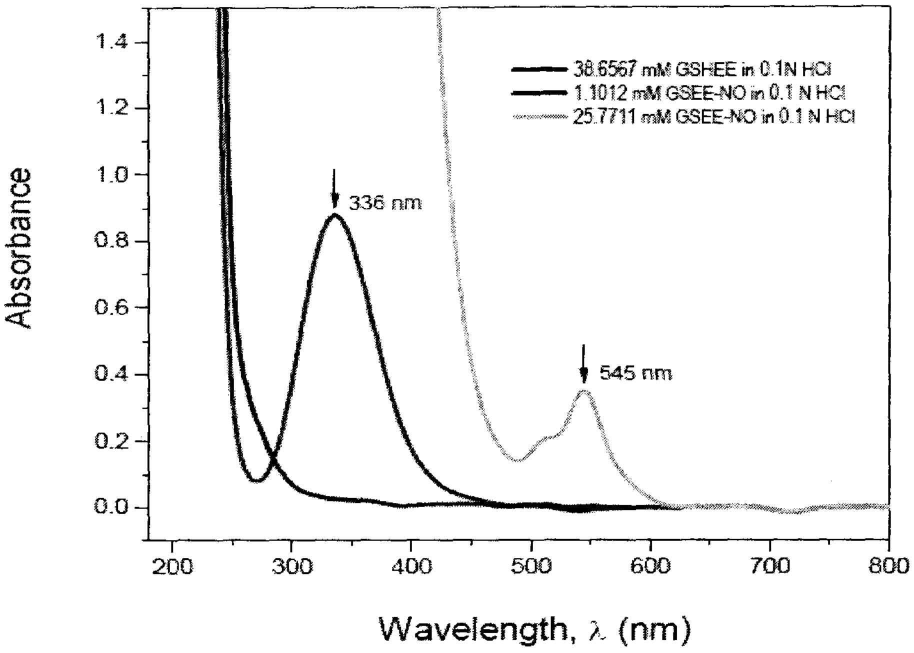
FIGS. 3A and 3B illustrates the UV-Vis spectra characterization of S-nitroso reaction of glutathione ethyl ester (GSHEE).
Figure 3:
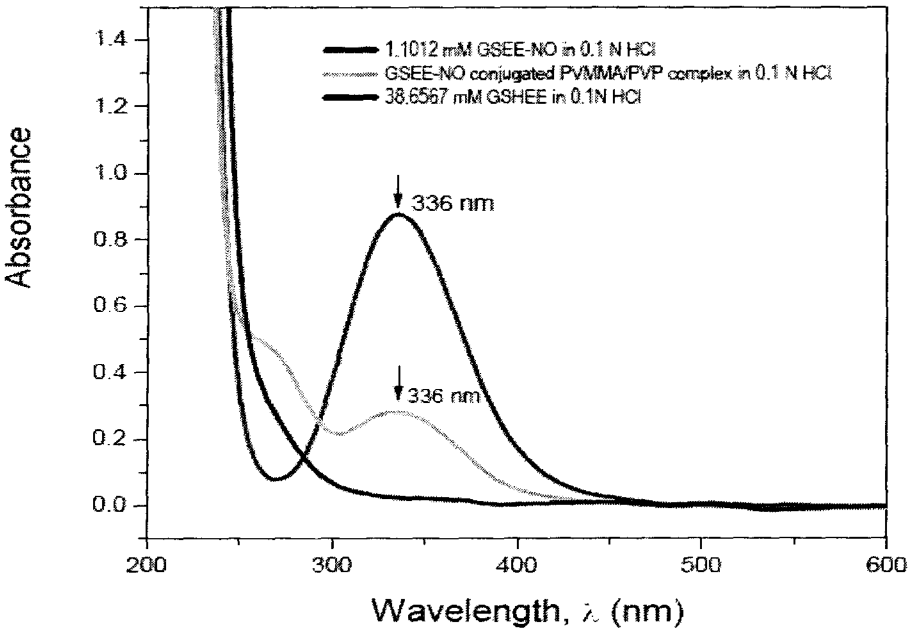
Figure 4:
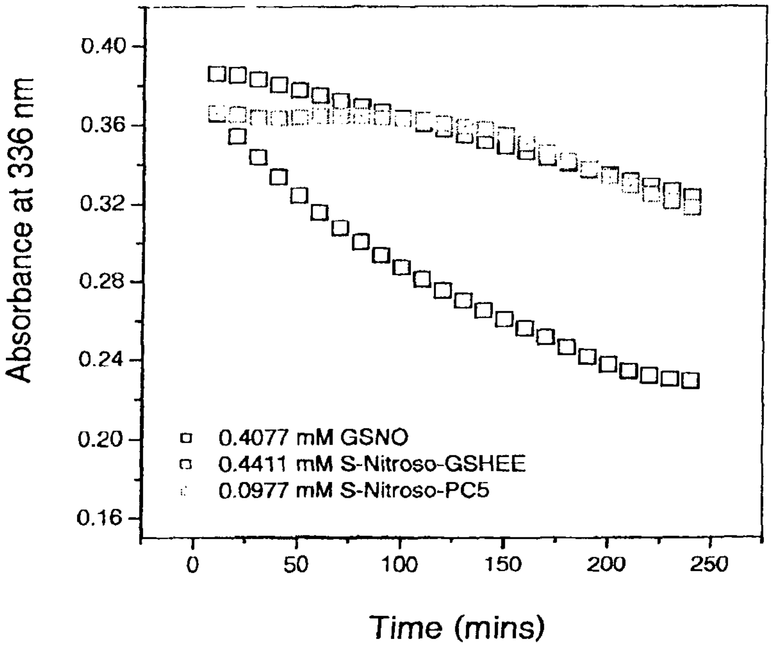
FIG. 4 illustrates the UV-Vis spectra of (a) pure PC5 (Phylochelatin); (b) S-nitrosation between PC5 and sodium nitrite; (c) S-nitrosoPC5 conjugated PVMMA/PVP complex in the aqueous medium.

The formation of S—NO group in both RSNO and RSNO-conjugated PVMMA/PVP complex can be demonstrated via the appearances of the characteristic absorbance of S—NO bond at $\lambda$=336 nm and $\lambda$=545 nm, corresponding to the maximum absorption in UV and visible range, respectively. This can be assigned to $\sigma\rightarrow\sigma^{\square}$ and $\pi\rightarrow\pi^{\square}$ electron transition. Spectral changes were recorded in the range 200-800 nm at room temperature using a Cary 50 UV-Vis Spectrophotometer (Varian Inc.). FIGS. 2, 3 and 4 demonstrate spectra changes when using GSNO, GSHEE and PC5 as RSNO species, respectively.

Example 5

Kinetics of NO Decomposition from RSNOs in Aqueous Medium

In this invention, GSHEE and phytochelatin are being used for the first time as NO donors. Their capability of carrying NO has been demonstrated in the aforementioned UV spectra. Their stability in aqueous medium was explored using the UV-Vis Spectrophotometer. Solutions of all RSNOs for this stability study were synthesized according to Example 1. Their decomposition kinetics in these solutions at room temperature was obtained from the time dependent absorbance changes at 545 nm in time intervals of 10 min.

Figure 5:
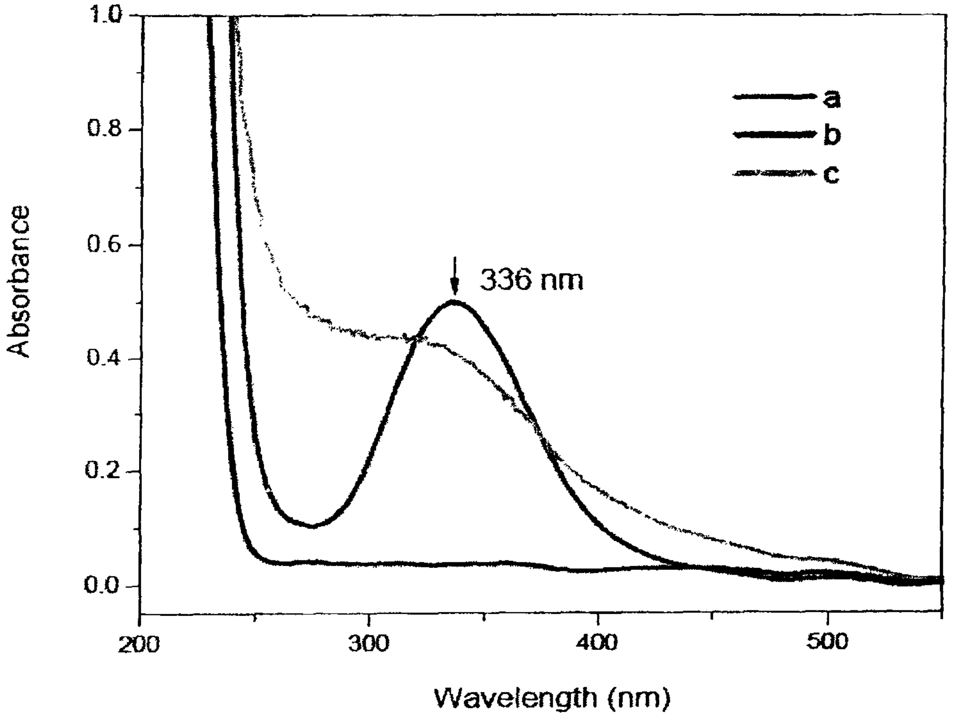
FIG. 5 shows the kinetics of NO decomposition in 0.1 N HCl from GSNO, S-Nitroso-GSHEE and S-Nitroso-PC5 respectively at 22° C.

FIG. 5 shows the profiles of NO decomposition kinetics for GSNO, S-Nitroso-GSHEE, and S-nitroso-PC5 at similar initial solution concentrations. A good linearity is obtained for all three curves, from the decay slopes, it can be seen that NO decomposition rate decreases in the order of GSNO>S-Nitroso-GSHEE>S-nitroso-PC5.

Example 6

FTIR Spectra

The conjugation of GSNO to PVMMA and hydrogen bonding interaction between PVMMA and PVP were characterized by Fourier transform infrared (FTIR) and the spectra recorded on a universal Attenuated Total Reflectance (ATR) Spectrum-One™ Perkin-Elmer spectrophotometer (Perkin Elmer, Conn., USA). All spectra were collected from a patch of samples at a resolution of 2 $cm^{-1}$ and were repeated three times. A background spectrum without any sample was subtracted from all spectra. The spectra were recorded from 4000~650 $cm^{-1}$.

Figure 6:
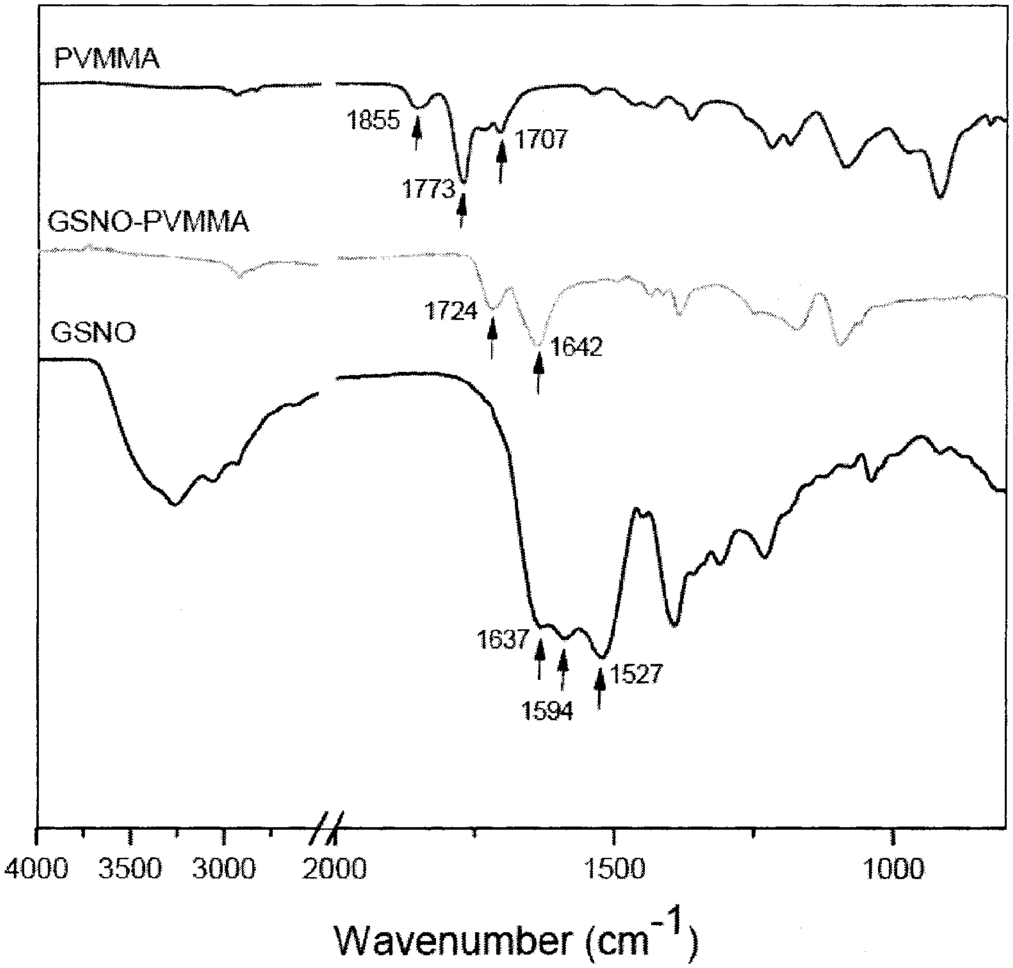
FIG. 6 presents the FTIR spectra of pure GSNO, pure PVMMA and GSNO-conjugated PVMMA film.

As shown in FIG. 6, the two shoulders at 1855 and 1773 $cm^{-1}$ typical for maleic anhydride cycles of pure PVMMA film has disappeared completely in the spectra of GSNO-conjugated PVMMA. The band at 1707 $cm^{-1}$, arising from a trace amount of carboxylic acid group in the raw material has been replaced by the presence of the carbonyl characteristic band at 1724 $cm^{-1}$, which can be attributed to the esterification between PVMMA and ethanol during the GSNO coupling process. Another major absorption features at 1642 $cm^{-1}$, characteristic for C═O group in the resultant amide group, has also appeared in the spectra of GSNO-conjugated PVMMA. This represents the occurrence of acylation reaction between anhydride group in PVMMA and the primary amino group in GSNO.

Figure 7:
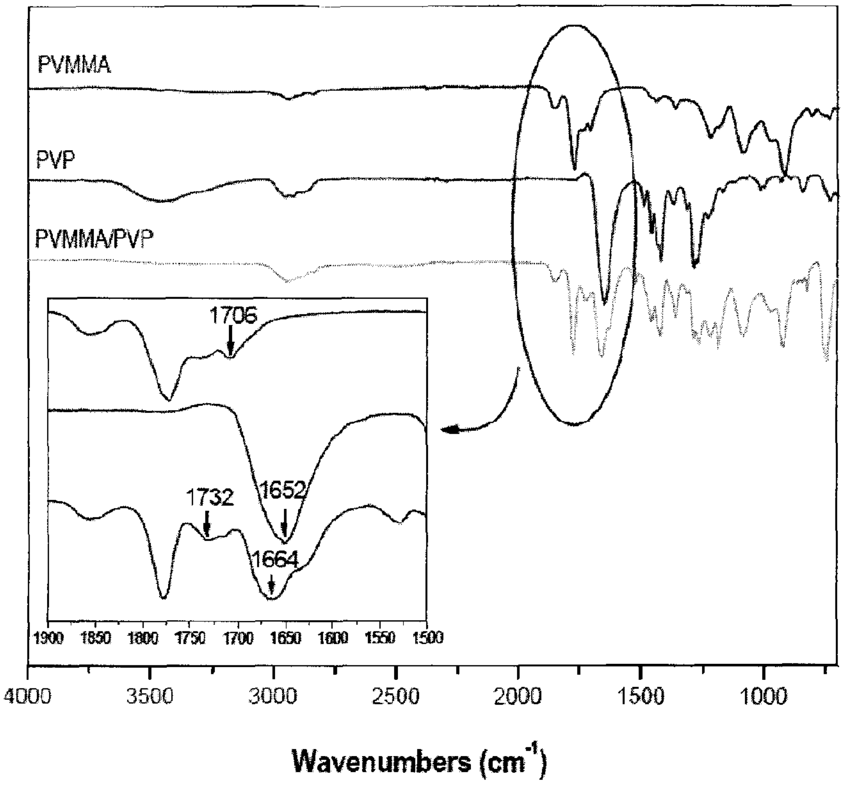
FIG. 7 presents the FTIR spectra of pure PVMMA, PVP and PVM/MA/PVP complex.

In FIG. 7, the free COOH group in pure PVMMA detected at 1706 $cm^{-1}$ can be ascribed to the stretching vibration of carbonyl group. After complex formation, the observed upward shift in this carbonyl stretching vibration frequency from 1706 to 1732 $cm^{-1}$ reflects an increase of "free" C═O groups due to the strong intermolecular hydrogen-bonding interaction upon the addition of PVP. Meanwhile, the band at 1652 $cm^{-1}$ in PVP, arising from cyclic imide group is also observed to shift to 1664 $cm^{-1}$ in PVMMA/PVP complex. These two band shifts are strong evidence supporting the complex formation involving hydrogen-bonding between acid O—H with imide oxygen in PVP molecules.

Example 7

NO In vitro Release Study

The in vitro release study was carried out by immersing 20 mg of RSNOs-PVMMA powders in 10 ml of 0.1 M PBS (pH 7.4) for extended periods of time. All samples were placed on a rotary shaker running at a speed of 15 rpm inside an incubator maintained either at room temperature or 37° C. At predetermined time intervals, 2 ml of NO-released medium was sampled and replaced with 2 ml of fresh PBS.

The NO release from RSNOs-PVMMA was quantified by the standard Griess assay. This colorimetric method is capable of quantifying all oxidized products of NO. NO is known to react readily with $O_2$ to produce $NO_2$, which then forms $NO_2^-$ and $NO_3^-$ in neutral aqueous solution according to the following reactions:

$$2NO+O_2\rightarrow 2NO_2 \quad \text{Equation (3)}$$

$$2NO_2+H_2O\rightarrow NO_2^-+NO_3^-+2H^+ \quad \text{Equation (4)}$$

Briefly, 1 ml of Griess reagent (NEDD) (0.1% w/v) plus 1 ml of sulfanilamide (1% w/v in 5% v/v $H_3PO_4$) at room temperature was incubated with an equal volume (1 ml) of sample. The UV absorbance of the resulting solution at 540 nm wavelength was determined and the total [$NO_2^-$] in the sample solution was calculated from the standard curve of 3-120 μmol/L $NaNO_2$, and the results expressed as μmol.

The in vitro release behavior of NO from RSNOs-PVMMA/PVP complex was carried out in the same manner as described above for RSNOs-PVMMA powders. 20 mg of RSNOs-PVMMA/PVP complex powder was immersed in 10 ml of 0.1 M PBS (pH 7.4) for extended periods of time. All samples were placed on a rotary shaker running at a speed of 15 rpm inside an incubator maintained at either the room temperature or 37 ° C. At predetermined time intervals, 2 ml of NO-released solution was sampled and replaced with 2 ml of fresh PBS. The NO concentration was determined by the Griess assay.

Scheme 7

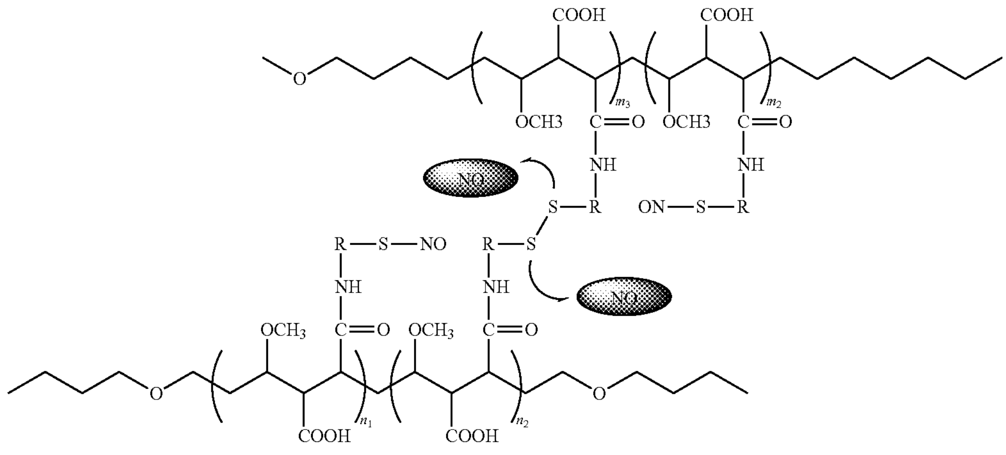

The NO release behavior from RSNOs-PVMMA conjugates is depicted in Scheme 7. As nitric oxide is gradually liberated from the complex, more disulfide bonds will form, giving rise to in-situ disulfide crosslinking between RSNO side chains which further reinforces the network structure of the complex. Based on the polymer structure and state of chain packing, different sustained and controllable release rate can be obtained by adjusting the component polymer molecular weight and concentration ratio, as well as the precipitation condition.

A. In vitro Release of NO from GSNO-PVMMA and GSNO-PVMMA/PVP Complex

Figure 8:
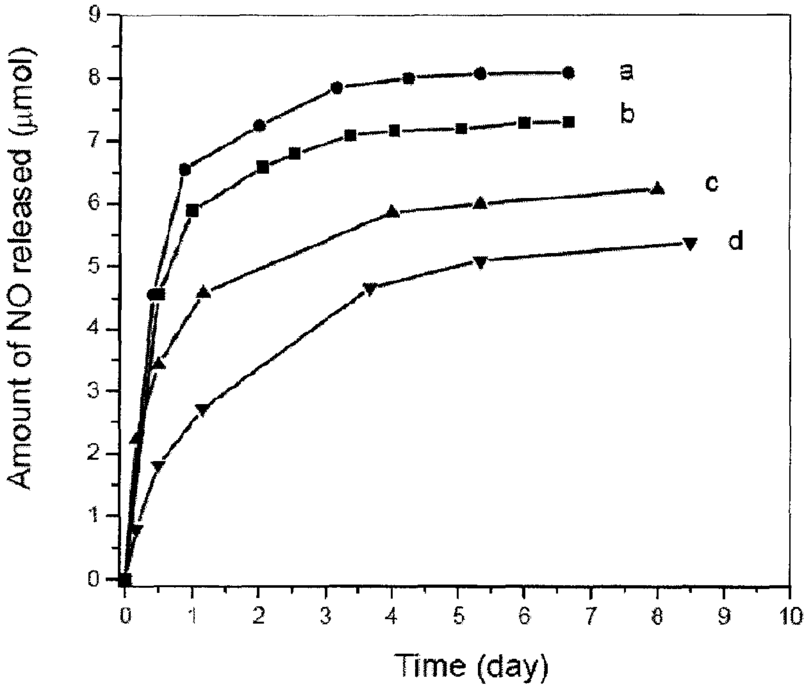
FIG. 8 shows the in vitro release behavior of NO from 20 mg GSNO-PVMMA conjugates in phosphate buffer saline at 37 (a) and 22° C. (b), and from GSNO-PVMMA/PVP supramacromolecular complexes containing 16.6 wt % of GSNO and 1:1 PVMMA/PVP weight ratio at 37 (c) and 22° C. (d).

As shown in FIG. 8, without forming the supramacromolecular complex with PVP, the release of NO from GSNO-PVMMA is relatively rapid with a release period only up to 3 days. In contrast, nitric oxide release rate can be significantly slowed down by the formation of supramacromolecular complex with PVP due to its decreased dissociation rate in an aqueous medium. A typical profile of such NO release can extend up to 9 days or more.

Figure 9:
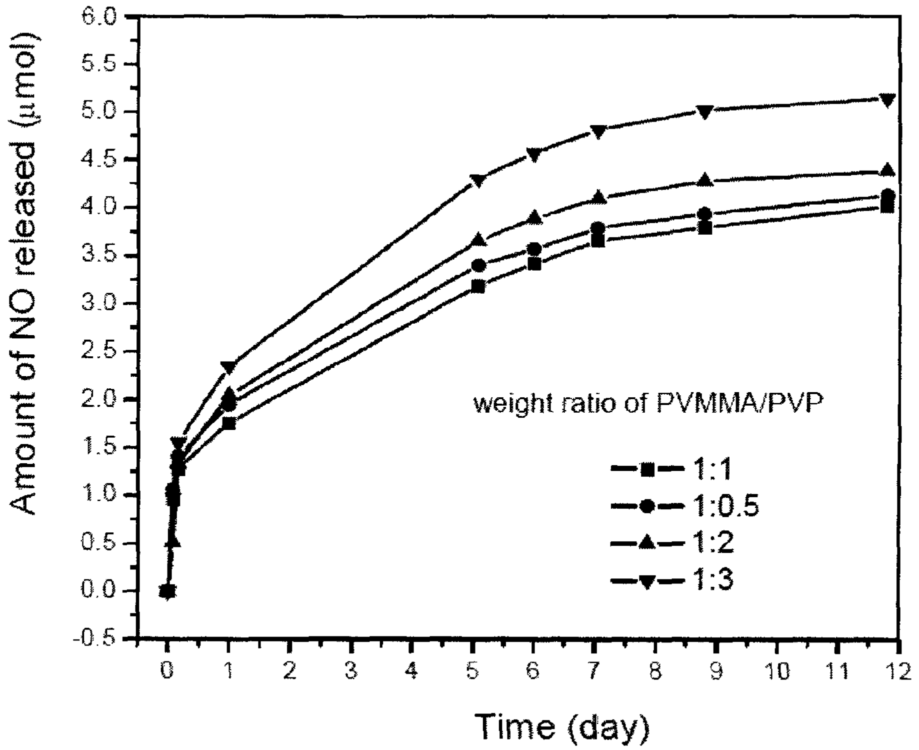
FIG. 9 shows the in vitro release behavior of NO from 20 mg GSNO-PVMMA/PVP supramacromolecular complexes containing 15.04 wt % of GSNO and different PVMMA/PVP weight ratio in phosphate buffer saline at 25° C.

B. In vitro Release of NO from GSNO-PVMMA/PVP Complex with Different Compositions Various weight ratios of PVMMA/PVP (1/0.5, 1/1, 1/2, 1/3) were investigated, As shown in FIG. 9, the NO release rate increases with increasing PVP content in the complex, but 1/1 ratio exhibits the slowest NO release rate which lasts at least 12 days.

C. In vitro Release of NO from GSNO-PVMMA/PVP Complex at Different Temperatures

Figure 10:
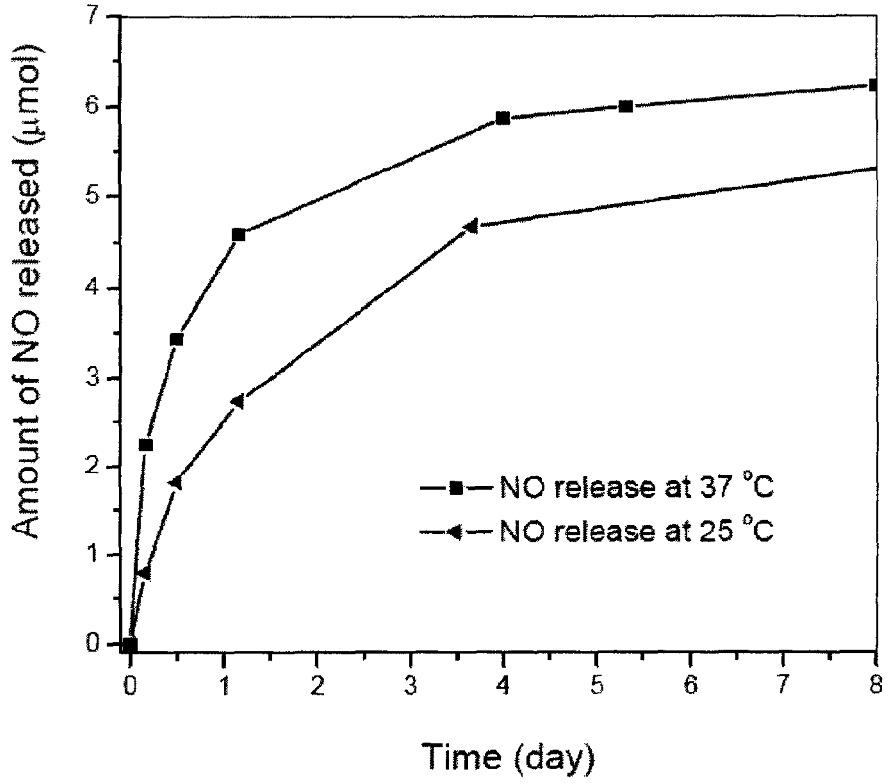
FIG. 10 shows the in vitro release behavior of NO from 20 mg GSNO-PVMMA/PVP supramacromolecular complexes containing 15.04 wt % of GSNO and 1:1 PVMMA/PVP weight ratio in phosphate buffer saline at 37 and 25° C.

FIG. 10 illustrates that temperature plays an important role in NO release from the present GSNO-PVMMA/PVP complex (1/1); higher temperature will significantly accelerate its release rate.

Figure 11:
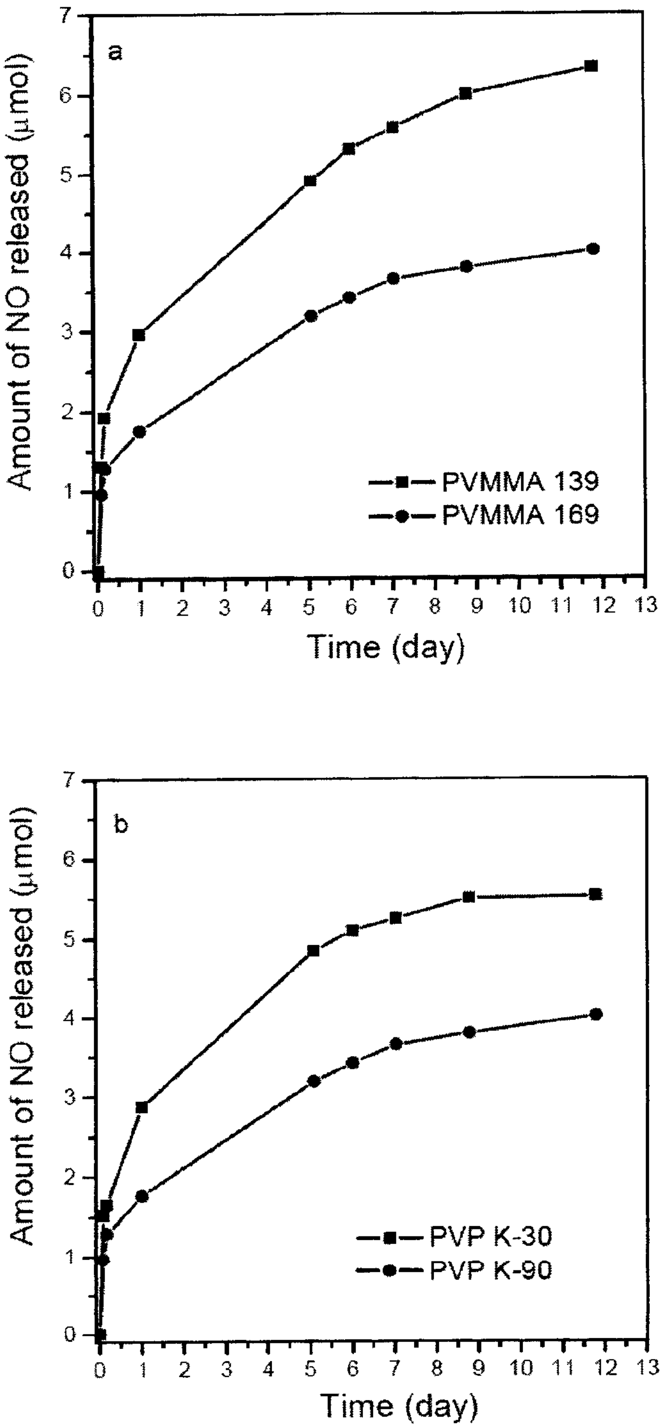
FIG. 11 shows the in vitro release behavior of NO from 20 mg GSNO-PVMMA/PVP supramacromolecular complexes containing 15.04 wt % of GSNO and 1:1 PVMMA/PVP weight ratio with different PVMMA (a) and PVP (b) molecular weight molecular in phosphate buffer saline.

D. In vitro Release of NO from GSNO-PVMMA/PVP Complex with Different Mw of PVMMA and PVP It is conceivable that higher molecular weight polymer will provide slower polymer dissolution due to the enhanced complex formation. FIG. 11 shows the effect of polymer molecular weight on the NO release behavior. The corresponding molecular weights of samples tested are listed in Table 1. It is evident from FIG. 11 that a smaller molecular weight of either PVMMA or PVP results in a faster NO release.

TABLE 1

| | Polymer | | | |
|---|---|---|---|---|
| | PVMMA Gantrez ® AN-139 | Gantrez ® AN-169 | PVP Plasdone ® K-29/32 | Plasdone ® K-90 |
| Molecular Weight | 1,000,000 | 1,980,000 | 58,000 | 1,300,000 |

Figure 12:
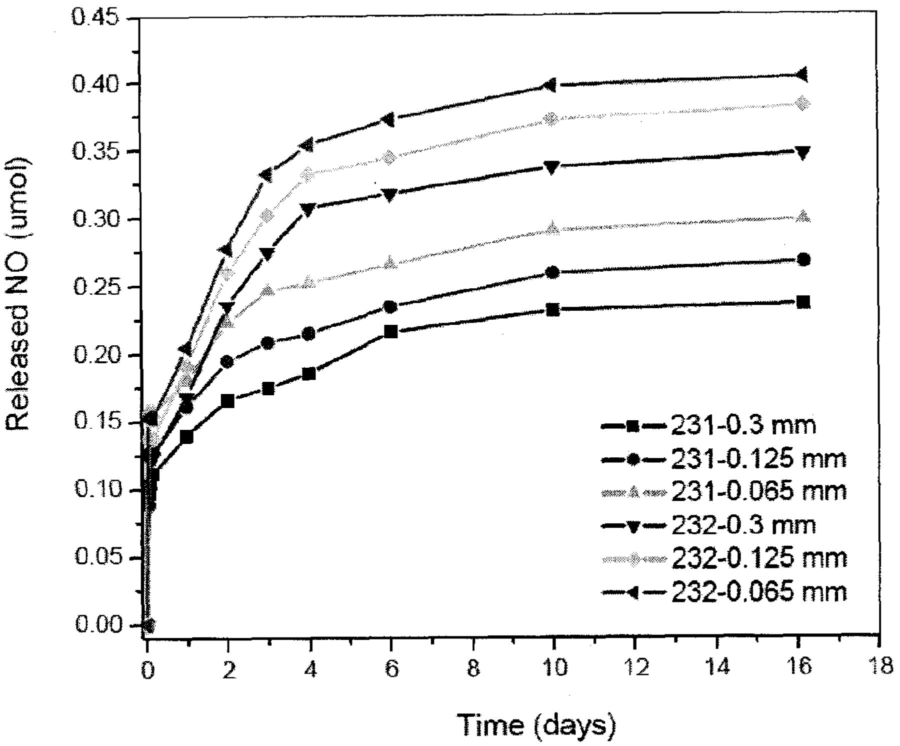
FIG. 12 shows the in vitro release behavior of NO from 20 mg GSNO-PVMMA/PVP supramacromolecular complexes with different particle size containing 7.52% (231 series) and 15.04 wt % (232 series) of GSNO and 1:1 PVMMA/PVP weight ratio at room temperature in phosphate buffer saline.

E. In vitro Release of NO from GSNO-PVMMA/PVP Complex with Different Particle Sizes The NO release patterns of GSNO-PVMMA/PVP complexes with three different average particle sizes (around 0.065, 0.125 and 0.3 mm, respectively) are presented in FIG. 12. It is clear that particle size plays an important role in the NO release behavior with smaller particle sizes leading to faster NO release rates.

F. In vitro Release of NO from S-NitrosoPC5-PVMMA/PVP Complex

Figure 13:
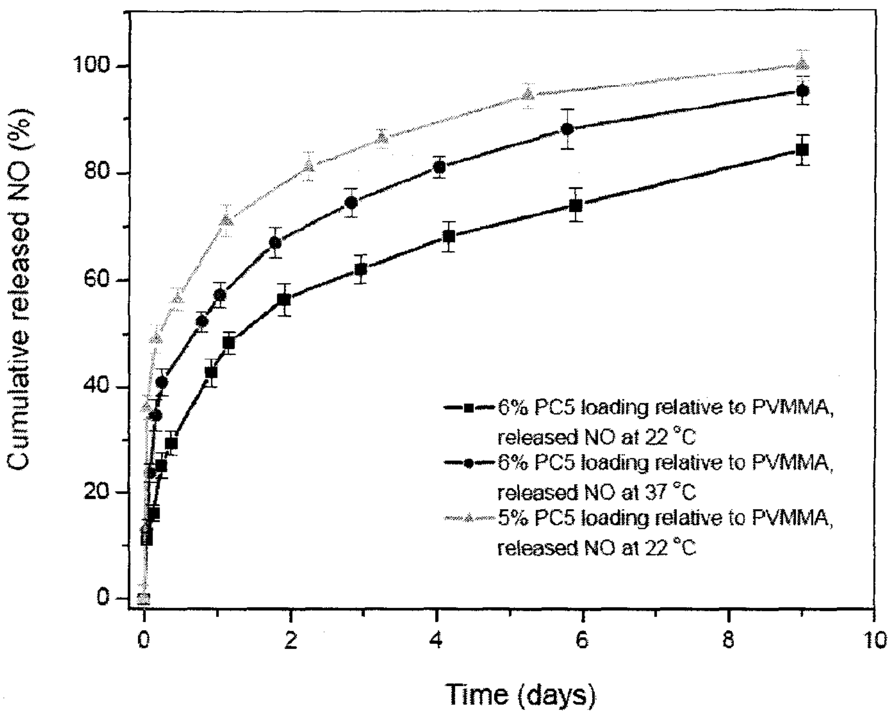
FIG. 13 shows the sustained in vitro release behavior of NO from S-nitrosoPC5 PVMMA/PVP supramacromolecular complex powder.

FIG. 13 demonstrates sustained NO release from S-NitrosoPC5-PVMMA/PVP complexes, where the release period can be extended up to at least 9 days. Again, it is seen that high temperature produces faster release, and the release rate can be controlled via adjusting the NO loading. Moreover, the selection of PC5 as the NO donor will allow for at least 90% of NO loading efficiency, which is greater than that of GSNO.

Example 8

Stability Study of GSNO-PVMMA/PVP Complex

A. Stability Under Room Conditions

Figure 14:
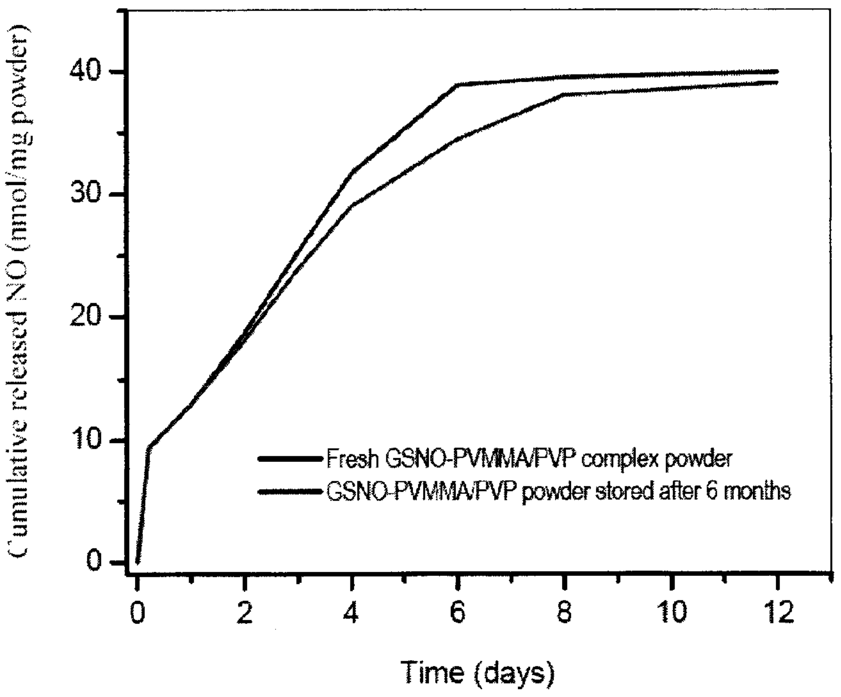
FIG. 14 compares the in vitro release behavior of NO from GSNO-PVMMA/PVP supramacromolecular complex powder before and after 6 months storage under room conditions.

GSNO-PVMMA/PVP Complex powder (see EXAMPLE 3A1) was stored in vials at RT (relative humidity: 22%.) for a duration of 6 months, without protection from light. From FIG. 14, it can be seen that there is no significant change in the NO release profile after this stability period. This suggests that the present GSNO-PVMMA/PVP complex is very stable when stored under room conditions.

B. Stability Under Irradiation

Figure 15:
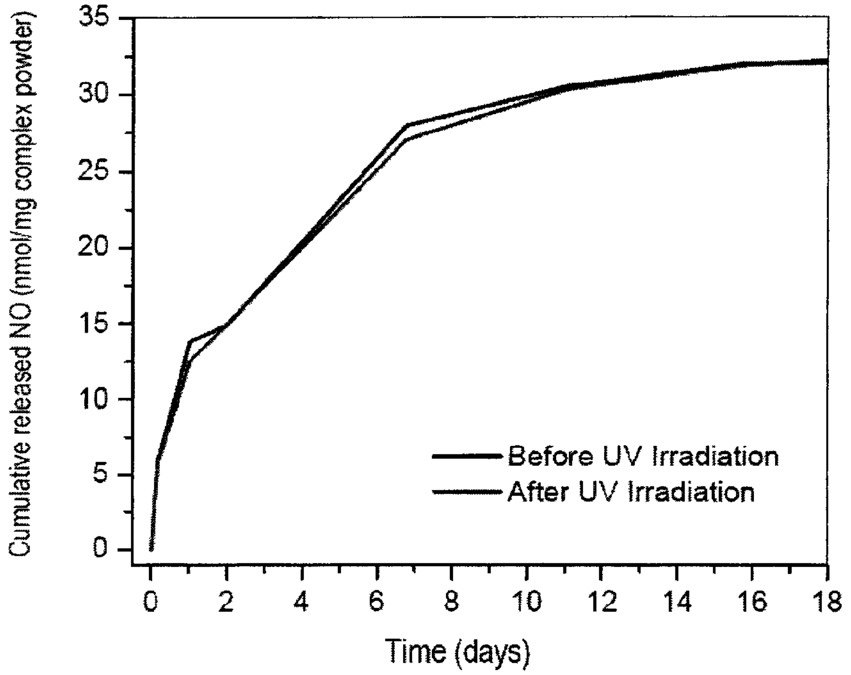
FIG. 15 compares the in vitro release behavior of NO from GSNO-PVMMA/PVP supramacromolecular complexes before and after UV irradiation.

GSNO-PVMMA/PVP Complex powder (see EXAMPLE 3A1) was exposed to UV Irradiation for 24 hours. FIG. 15 shows that the GSNO-PVMMA/PVP Complex is stable after undergoing short term UV irradiation.

Preparation of GSNO-PVMMA/EC Complex in the Nanofiber Form Via Electrospinning Apparatus Electrospinning has been widely applied to fabricate polymeric nonwoven, porous, and three-dimensional scaffolds containing fibers ranging in diameters from micrometer to nanometers. This one-step technology offers the potential for controlling the composition, structure and mechanical properties of biomaterials. In particularly, this method allows for the incorporation of drug molecule into soft fibers, which is ideally suited for wound dressing owing to their high water vapor permeability, good mechanical strength and excellent flexibility. In this process, drug loading and the preparation of final formulation can be accomplished in one step. In particular, through proper material selection and fiber structure design, the resulting material can be endowed with additional desirable properties such as bioadhesiveness, elasticity and capability of controlled drug release. In the present invention, RSNOs-loaded NO delivery systems based on nanofibers can be prepared form concentrated solutions by this method.

Example 9

Preparation of Stock Solution for Electrospinning

A. Preparation of PVMMA/EC Blend 2 g PVMMA and 1 g ethyl cellulose (EC) were dissolved in 15 ml of mixture of N-dimethylformamide (DMF) and acetone (volume ratio=2:3) separately. A series of PVMMA/EC blend solutions with weight ratios ranging from 1:0, 2:1, 1:1, 1:2 to 0:1 were successively obtained through the homogeneously blending of the two solutions.

B. Conjugation of GSNO to PVMMA/EC Blend

Around 308 mg of GSH was allowed to react with 69 mg of $NaNO_2$ in 1 ml of mixture of deionized water and ethanol (volume ratio=1:1) under room temperature. Immediately thereafter, the resultant pink GSNO solution was slowly dropped into the above described polymer solution under vigorous stirring to give a stable pink emulsion, which became clear after continuous stirring for additional 20 min.

Example 10

Electrospinning of GSNO-PVMMA/EC Blend Solution

The above blend solution was filled into a 5 ml syringe with a flat-tipped stainless-steel gauge 20 needle as the nozzle. In a typical procedure, the GSNO-PVMMA/EC blend solution was fed at a rate of 0.2~0.8 ml/h using a syringe pump (KDS 200, KD Scientific, USA) located in a horizontal mount. A high voltage (12~18 kV) was applied between the nozzle and grounded aluminum collector using a high voltage power supply (EL 50PO.8, Glassman High Voltage Inc., USA). The distance between the tip and collector was adjusted from 12 to 16 cm. To minimize the photo- and thermo-sensitivity of GSNO, the entire set up was placed in a fume hood which was out of direct light and kept at 20° C. to reduce the NO loss during the process. All as-spun fabrics were stored in a desiccator protected from direct light and refrigerated at 4° C. before subsequent use.

Example 11

Morphological Characterization of As-Spun Mats

Figure 16:
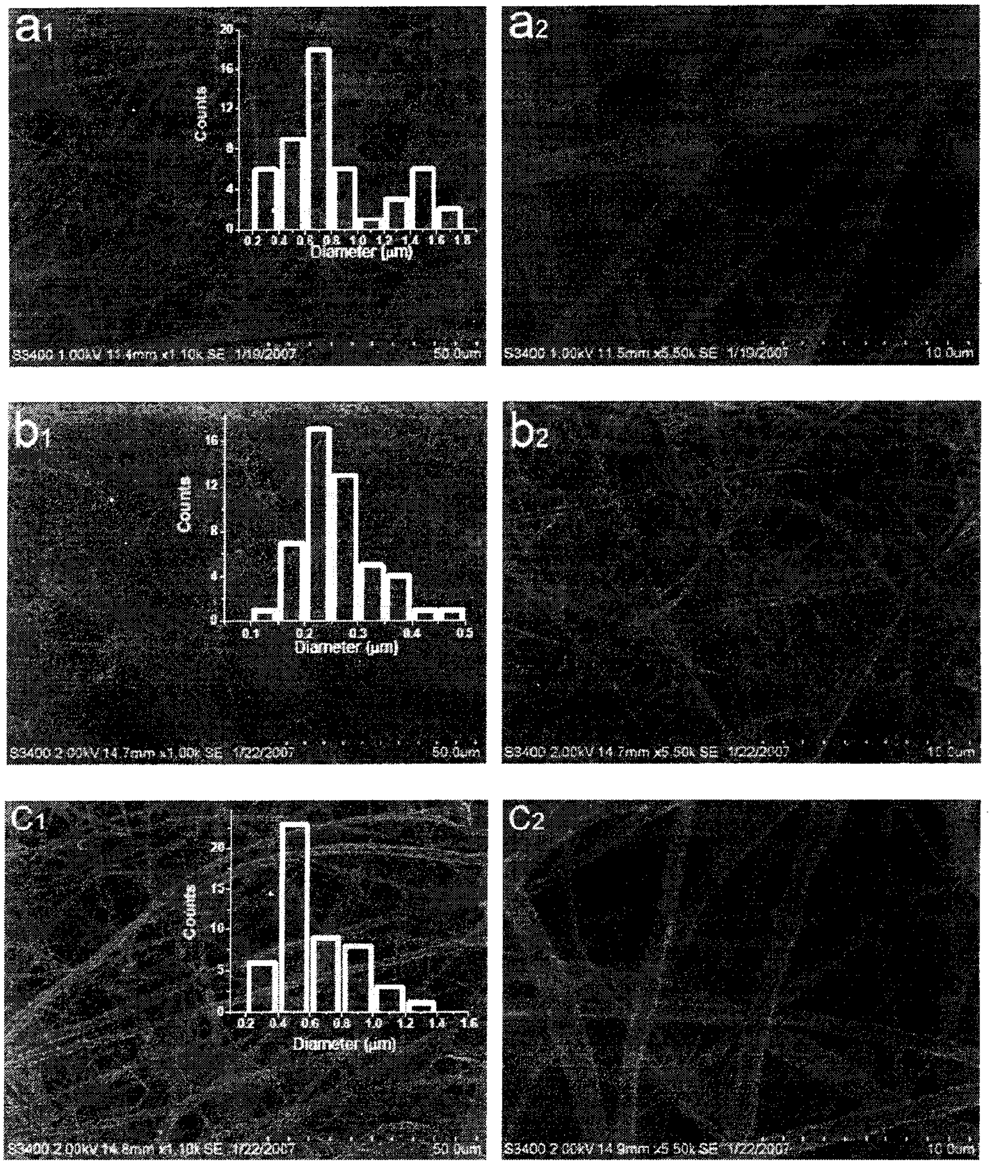
FIG. 16 shows representative SEM photographs of nanofibers electrospun from ($a_1$, $a_2$) 12 wt % GSNO-conjugated pure PVMMA; ($b_1$, $b_2$) pure EC; ($c_1$, $c_2$) GSNO-conjugated PVMMA/EC with 1:1 polymeric composition at low and high magnification, respectively.

The morphological appearance and size distribution of as-spun fabrics were investigated by an environmental scanning electron microscope (HITACHI S-3400N SEM, Japan) with an accelerating voltage of 1 kV and 2 kV. FIG. 16 shows the SEM images of nanofibers spun from GSNO-PVMMA (at concentration of 13.33 wt %), EC (at concentration of 6.67 wt %), and GSNO-PVMMA/EC composite. The insets in the survey images display the corresponding fiber size distributions. The average diameters of GSNO-conjugated PVMMA and EC ultrathin fibers are 0.82 μm and 0.25 μm, respectively, and the composite nanofiber shows an intermediate average diameter of 0.64 μm.

Figure 17:
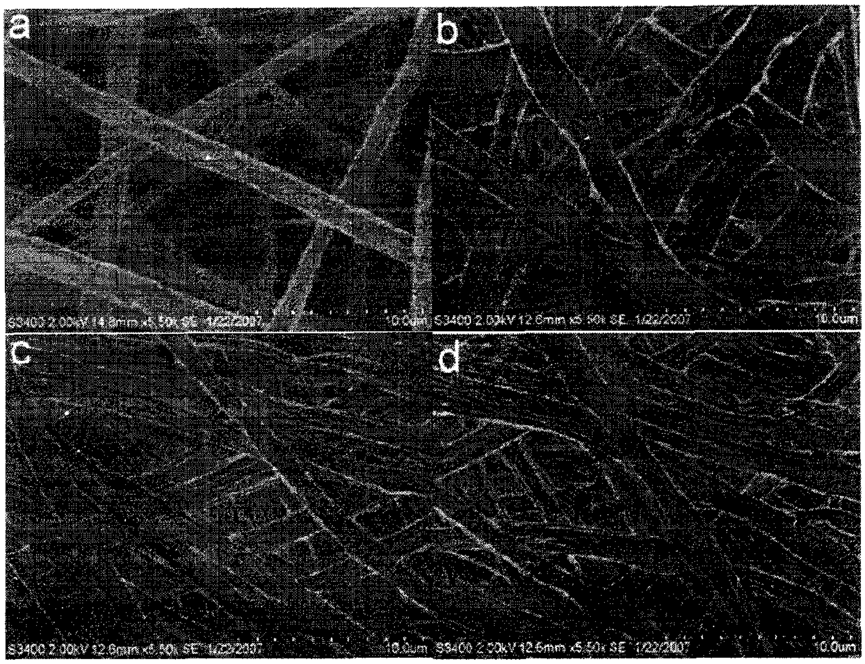
FIG. 17 is the SEM pictures of dried 1:1 PVMMA/EC electrospun fabrics with 12% GSNO loading before (a) and after (b) 1 hour; (c) 1 day and (d) 3 days of immersion in PBS at 37° C.

PVMMA is a typical erodable polymer, and the elelctrospun nanofibers based on pure PVMMA alone will dissolve more quickly than casting films in PBS at 37° C., thus presenting a major limitation for its application to wound dressing. The addition of EC in PVMMA/EC nanofibers significantly improves the integrity of as-spun fabrics in water. As shown in FIG. 17, the membrane made of 1:1 GSNO-PVMMA/EC nanofibers retained its fibrous structure after 3 days immersion in water at 37° C. There is virtually no change in fiber morphology between Image c and d suggesting that the addition of EC could endow the nanofibers with extended capability of remaining its integrity, which is desired for wound dressing.

Example 12

FTIR Spectra

The hydrogen bonding interaction in the GSNO-PVMMA/EC system, as illustrated in Scheme 8, was characterized by Fourier transform infrared (FTIR). The spectra were recorded on a universal Attenuated Total Reflectance (ATR) Spectrum-One™ Perkin-Elmer spectrophotometer (Perkin Elmer, Conn., USA) from 4000~650 $cm^{-1}$. All spectra were collected from a patch of samples at a resolution of 2 $cm^{-1}$ and were repeated three times. A background spectrum without any sample was subtracted from all spectra.

Scheme 8

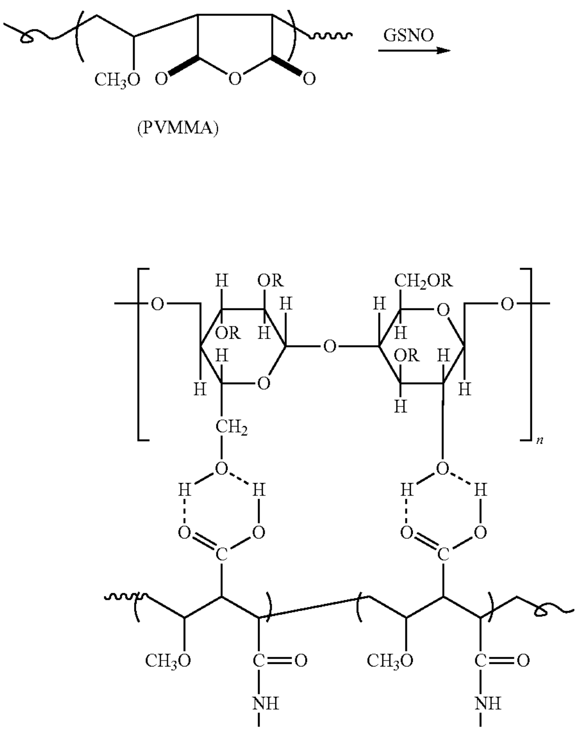

(PVMMA)

-continued

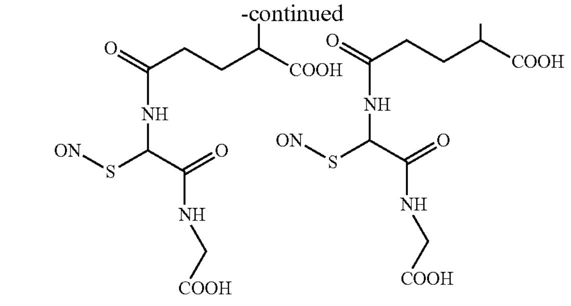

(GSNO-PVMMA)

(EC, R = —H, —$CH_2CH_2$)

Figure 18:
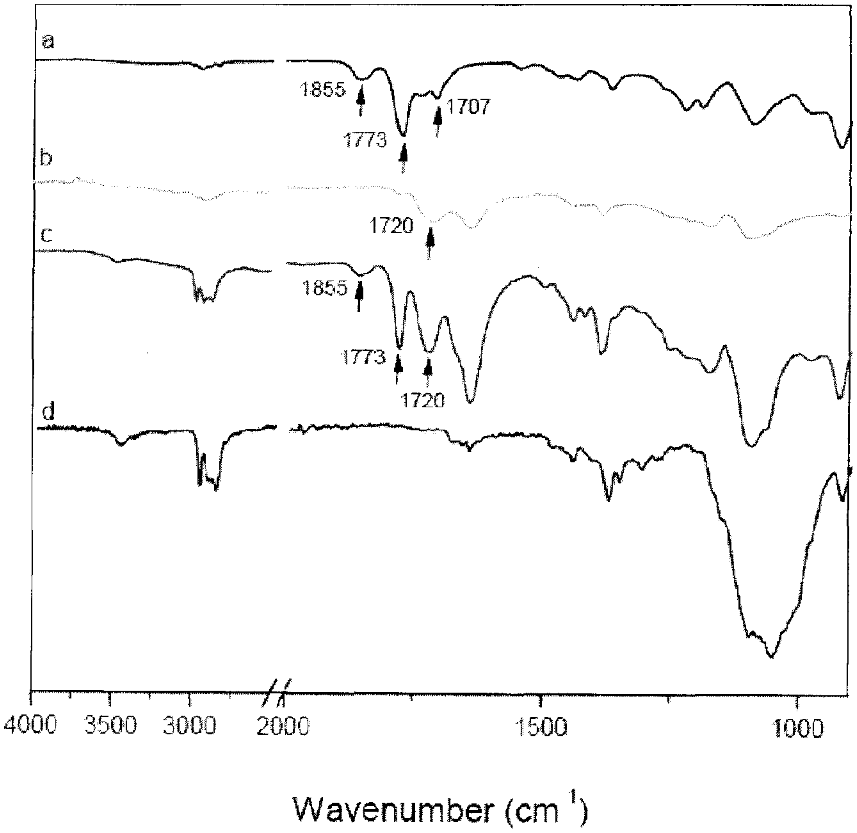
FIG. 18 is the 1' FIR spectra of as-spun (a) pure PVMMA, (b) GSNO-conjugated PVMMA/EC, (c) GSNO-free PVMMA/EC and (d) pure EC nanocomposite fabrics.

From FTIR spectra of pure PVMMA in FIG. 18, a trace carboxyl group, ascribed to the stretching vibration of carbonyl group at 1707 $cm^{-1}$, may result either from the slight hydrolysis during the nanofiber formation process or from the raw materials. The apparent upward shift from 1707 to 1720 $cm^{-1}$ in the carbonyl stretching frequency in the PVMMA/EC film sample reflects an increase of "free" C═O groups due to the strong intermolecular hydrogen-bonding interaction upon the addition of EC. Additionally, the absorbance peaks at 1855 and 1773 $cm^{-1}$ typical of anhydrides are still prominent in the PVMMA/EC blend films.

Example 13

Micro-Tensile Test of As-Spun Fabrics

Figure 19:
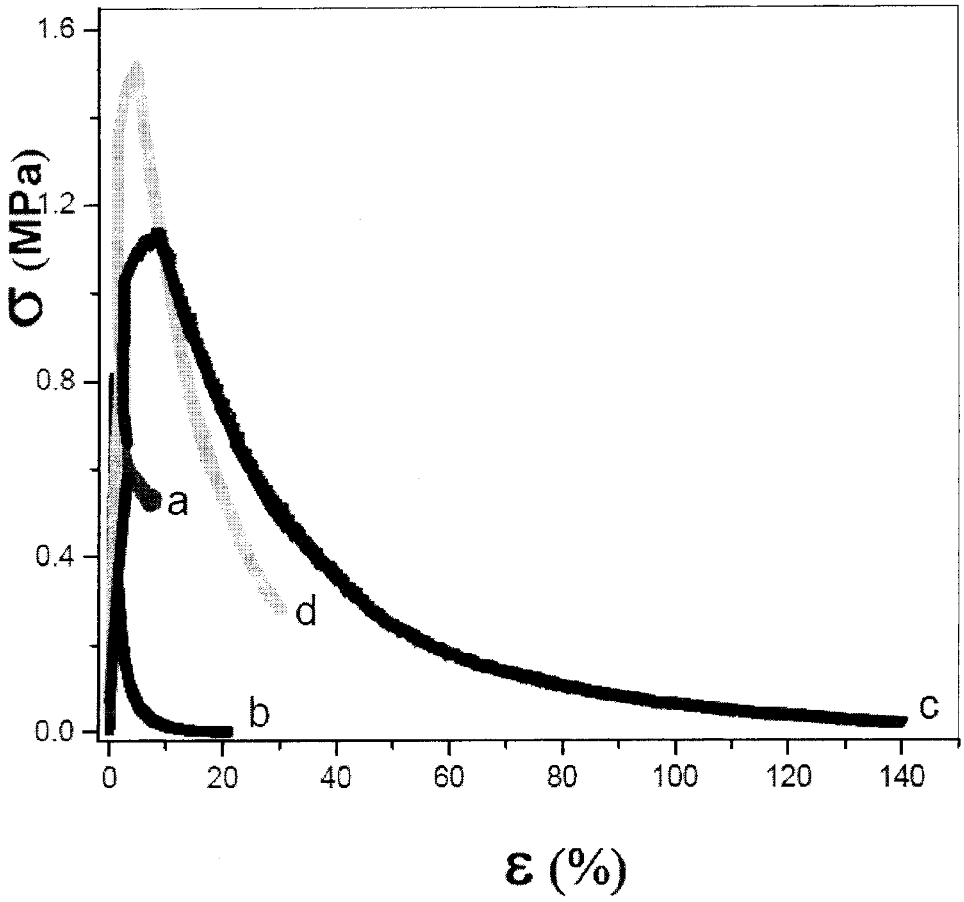
FIG. 19 shows the mechanical properties of the as-spun fiberious mats. (a) pure PVMMA; (b) pure EC; (c) GSNO-fret PVMMA/EC (1:1) and (d) 12 wt % GSNO-conjugated PVMMA/EC (1:1).

The mechanical properties of GSNO free and incorporated PVMMA/EC electrospun fabrics were evaluated using a texture analyzer (TA.XTplus, Stable Micro Systems, Haslemere, Surrey, UK) equipped with a 5 kg load cell. In the stretch test, electrospun fiber mats with even thickness was cut into 30×20 mm sample pieces. A sample was held between two clamps for this test. During measurement, the film was pulled by the top clamp at a rate of 0.5 mm/s until rupture. The force and elongation were recorded automatically by the instrument. Each measurement was repeated four times and the results are presented in FIG. 19. It is clear from FIG. 19 that the PVMMA/EC and GSNO-PVMMA/EC films exhibit significantly enhanced mechanic strength over that of the mono-component PVMMA or EC films. This improvement can be attributed to the hydrogen-bonding interaction between PVMMA and EC.

Example 14

In vitro Release of NO from As-Spun Mats

The in vitro NO release study was carried out by immersing a 20 mg electrospun mat (~2×2 $cm^2$) in 10 ml of 0.1 M PBS for an extended period of time. All samples were placed on a rotary shaker inside an incubator maintained at 37° C. At predetermined time intervals, 5 ml of the release medium was sampled and replaced with 5 ml of fresh PBS.

Figure 20:
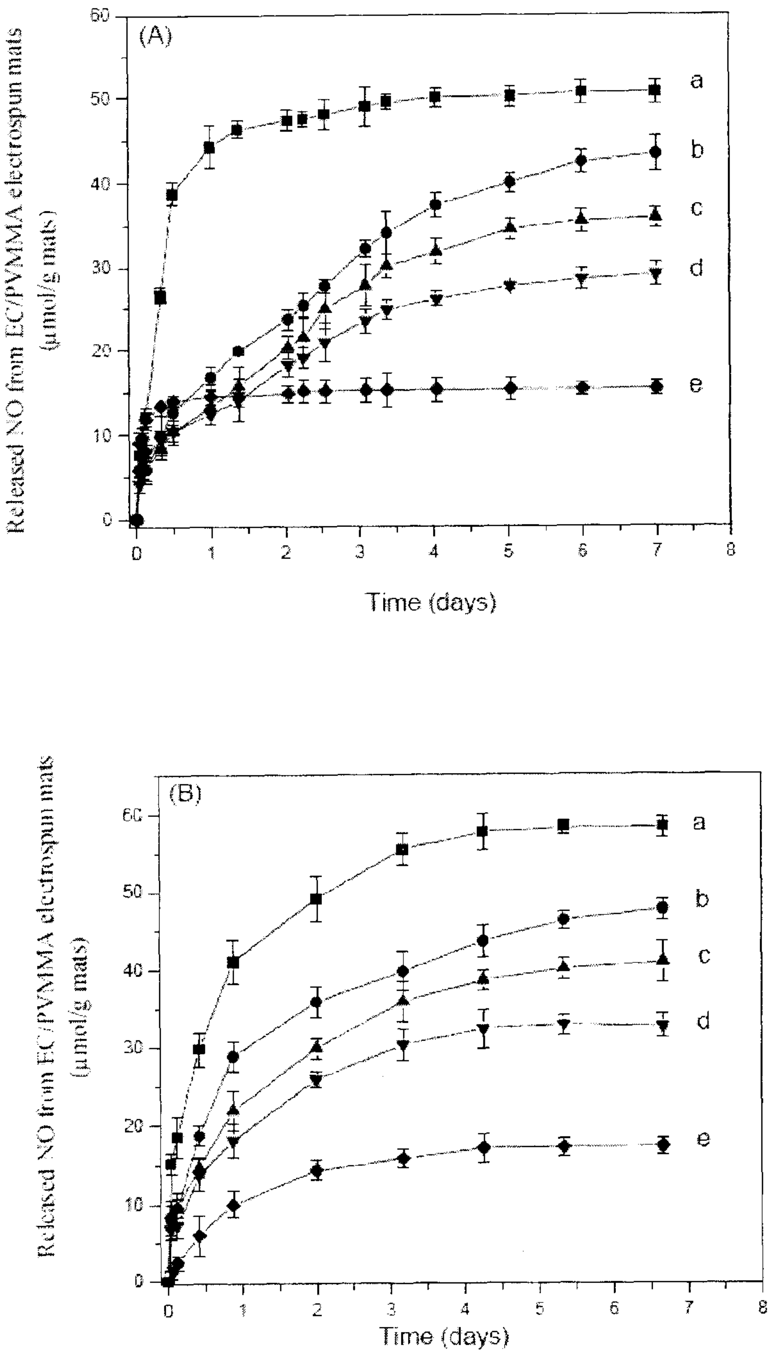
FIG. 20 shows the effect of composition on in vitro release rate of NO from 12% GSNO incorporated PVMMA/EC electrospun mats in 0.1 M PBS (pH 7.4) at (A) room temperature and (B) 37° C. (a) Pure PVMMA; (b) 2:1 PVMMA/EC; (c) 1:1 PVMMA/EC; (d) 1:2 PVMMA/EC; (e) Pure EC.

The NO release from the fiber mat was quantified by the Griess assay described in Example 7. The results of NO release in pH 7.4 buffer from as-spun nanofibers of different compositions are presented in FIGS. 20A and 20B for the room temperature and 37° C., respectively. It can be seen that the NO release rate from GSNO-PVMMA/EC (1:1) is around 35 to 40 μmol/g mats depending on temperature and the NO release is significantly slowed down with increasing EC content. The composite films show a prolonged release period of over 1 week.

Preparation of RSNOs-PVMMA Loaded Microspheres Using an Ultrasonic Atomizer Apparatus Ultrasonic atomization has been applied widely to spray drying, microencapsulation and substrate coating. This one-step method can effectively produce more precise, uniform microspheres and thin film coatings. Droplets sprayed from a single or dual-feed nozzle can be solidified in air as well in a collecting bath. Unlike electrospinning method which is applied to concentrated polymer solution, this method is particularly suitable for diluted polymer solution. In the following examples, production of microspheres based on RSNOs-loaded supramacromolecular complexes will be illustrated via this method.

Example 15

Ultrasonic Spraying of GSNO-PVMMA (Gantrez® AN 139)/P(VP/VAc) (Plasdone® S-630) Blend Solution Supramacromolecular NO-releasing complexes based on low molecular weight PVMMA (Gantrez® AN 139) and Poly(vinyl pyrrolidone-co-vinyl acetate) (Plasdone® S-630) with molecular weight of $1.0\times10^6$ and $2.4\times10^4$, respectively, were selected for this example. Microspheres containing GSNO-PVMMA as NO prodrug were prepared according to the following procedures.

1 g P(VP/VAc) was allowed to dissolve in 40 ml acetone, 1 g PVMMA was dissolved in 10 ml acetone, 1 ml GSNO (see Example 1A) was conjugated to this PVMMA (see example 2A1), the resulting GSNO-PVMMA solution was diluted into the mixture of 40 ml acetone and 10 ml ethanol, which subsequently was blended with P(VP/VAc) solution.

The final solution was pumped through the inlet of an ultrasonic nozzle (SONO-TEK Corp. 8700-60 MS) driven by a syringe pump ((KD-Scientific, Model 200) at a flow rate of 0.5 ml/min while the ultrasonic generator was operating at 5.0 w power. The sprayed mist was air dried during its settling through a glass column (15 cm diameter and 60 cm height).

Figure 21:
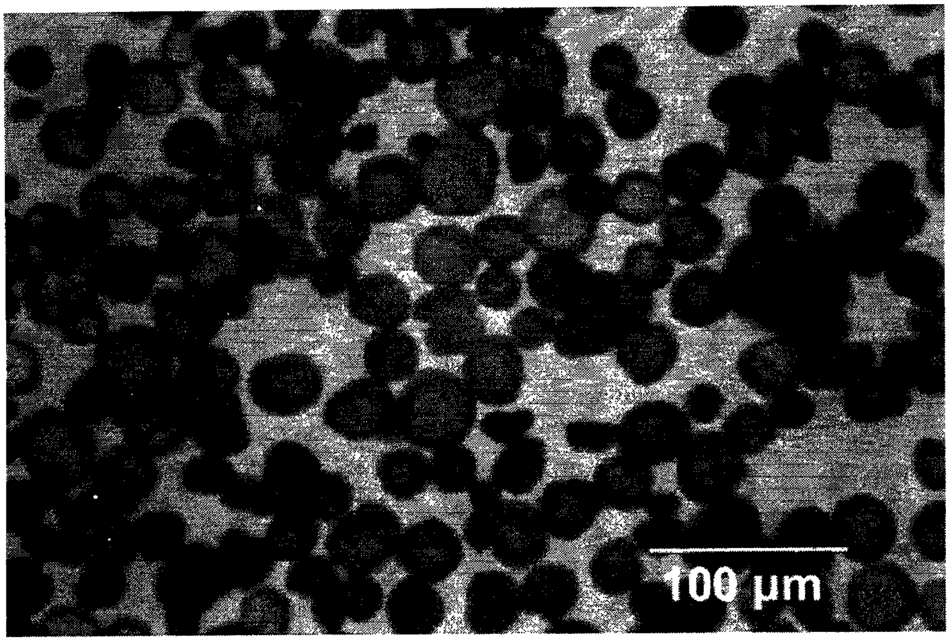
FIG. 21 shows the photomicrograph of GSNO-PVMMA (AN139)/P(VP/VAc) microspheres prepared by ultrasonic atomization method.

The dried microparticles were collected and morphologically characterized under a microscope. FIG. 21 shows the size and shape of the particles collected corresponding to completely solidified microspheres.

Example 16

Ultrasonic Spraying of GSNO-PVMMA (Gantrez® AN 169)/Ethyl Cellulose (Ethocel® NF100) Blend Solution Supramacromolecular NO-releasing complexes based on high molecular weight PVMMA (Gantrez® AN 169) (Mw: $1.98\times10^6$) and ethyl cellulose (Ethocel® NF100) (ethoxy content, 48.8% DS; viscosity, 100 cP for 5% solution in 80% and 20% alcohol), respectively, were selected for this example. Microspheres containing GSNO-PVMMA as NO prodrug were prepared according to the following procedures.

Initially, 500 mg ethyl cellulose was homogeneously dissolved in 40 ml acetone, giving a concentration of 1.25%. Meanwhile, 500 mg PVMMA was dissolved in 10 ml acetone, 1 ml GSNO (see Example 1A) was conjugated to this PVMMA (see example 2A1), the resulting GSNO-PVMMA solution was diluted into a mixture of 40 ml acetone and 10 ml ethanol, which subsequently was blended with ethyl cellulose solution.

The final solution was pumped through the inlet of ultrasonic nozzle (SONO-TEK Corp. 8700-60 MS) driven by a syringe pump (KD-Scientific, Model 200) at a flow rate of 0.5 ml/min while the ultrasonic generator was operating at 5.0 w power. The sprayed mist was air dried during its settling through a glass column (15 cm diameter and 60 cm height).

Figure 22:
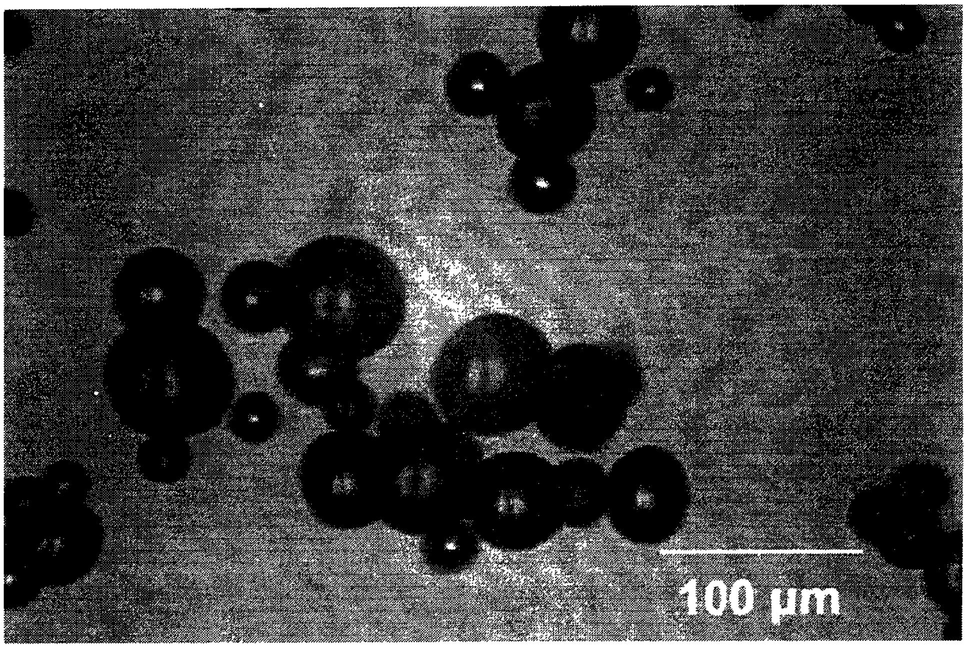
FIG. 22 shows the photomicrograph of GSNO-PVMMA (AN169)/EC microspheres prepared by ultrasonic atomization method.

The dried microparticles were collected and morphologically characterized under a microscope. FIG. 22 shows the size and shape of the particles collected, corresponding to completely solidified microspheres.

Example 17

Preparation of GSNO-PVMMA/PVP Ultrathin Coating Via Layer-by-Layer Assemblies

The ultrathin complex coating was fabricated according to the following procedures. Firstly, 0.025 mM GSNO-PVMMA solution was prepared according to Example 2A, and 0.02 mM PVP solution was made by dissolving 1.3 g of PVP in 50 ml mixture of acetone and ethanol (4/1 volume ratio). To maintain their solution concentrations, these two solutions were placed in an ice bath during the whole coating procedure.

Next, substrates (glass slide and PTFE sheet) were firstly exposed to PVP solution for 10 mins, then sequentially immersed in three baths of the solvent mixture of acetone and ethanol for a total of 4 mins to wash off the excess PVP polymer. Immediately thereafter, the substrates were exposed to the GSNO-PVMMA solution for 10 mins, followed by immersion sequentially in three baths of acetone solution for a total of 4 mins. The cycle was repeated for 20 bilayers, which can be continued to desired thickness. Following this assembly process, the coated substrates were air dried and stored in a dissector under room conditions.

Example 18

In vivo Evaluation of GSNO-PVMMA/PVP Complex Powder

A. Materials and Methods

It is well-known that chronic wounds such as diabetic ulcers often suffer from impaired wound healing. Recent evidence suggests that NO may play a critical role in wound healing especially in the healing process of diabetic foot ulcers which is characterized by a reduced NO level in the wound tissue. The exogenous NO supplementation with NO donor DETA NONOates and L-arginine has been shown to enhance wound healing in diabetic rats [32, 33]. In our case, a diabetic rat model was used for assessing the benefit of RSNOs-PVMMA/PVP supramacromolecular complex systems (obtained from Example 3A1) in wound healing. The experiments described below were performed to determine (1) if NO can be continuously generated from GSNO conjugated PVMMA/PVP complex powder and (2) if this NO containing powder formulation can enhance wound healing in a diabetic rat model. All of the experiments were performed under an animal protocol approved by the The University of Toronto Animal Care Committee.

B. Induction of Acute Diabetic Mellitus

15 Male Sprague-Dawley rats (from Charles River, Montreal) were acclimatized for one week, given food and water ad libitum. 7 days before wounding, the animals were injected intraperitoneally (IP) with streptozotocin (60 mg per kg body-weight in citrate buffer 0.1 mol/L, pH 4.5) to induce diabetes. Evidence of diabetes was confirmed by blood glucose levels greater than 14 mmol/L and frequent urination. Four animals not achieving the diabetic state after 24 hours were reinjected with streptozotocin and one of them was excluded from the study because the blood glucose level remained below 14 mmol/L. After the induction of diabetics, the blood glucose level were monitored twice a week to ensure that the diabetic state was remained throughout the entire wound healing experiment.

C. Surgical Procedures

On the day before surgery, animals were weighed and assigned to two groups (7 for control group and 8 for test group). The following procedures were conducted while animals were anesthetized with isoflurane inhalation. Firstly, the dorsal surface was shaved, the skin was washed with povidone-iodine solution and 70% alcohol. Rats were given analgesic (ketoprofen, 3 mg/kg, S.C.) immediately before surgery. Subsequently, a full thickness excisional wound was created by removal of the skin and panniculus carnosus using a 8 mm biopsy punch. At the wound sites, the control group was treated with 20 mg blank PVMMA/PVP complex powder without NO loading, the test group was treated with 20 mg GSNO-PVMMA/PVP complex powder (from example 3A1). All polymer powders quickly adhered to the wound tissue with the assistance of a few drops of sterile saline.

After application of the polymer powder, tincture Benzodine Compound (Xenex Laboratories, Ferndale, Wash.) was applied at the surrounding skin and wounds were covered with semi-occlusive polyurethane dressings (Tegaderm™, 3M, St. Paul, Minn.). Afterwards, Animals were transferred to individual cages and maintained on a standard diet, allowed free access to water ad libitum.

D. Post-Operation Wounds Treatment

During the first 7 days after wounding, Tegaderm dressing was changed everyday while the animals were anesthetized with isoflurane inhalation, and photographs of the wound sites were recorded using a digital camera. A calibration scale was recorded with each photograph. From the 7$^{th}$ day after injury on, the wounds were no longer closed with a dressing.

TABLE 2

| Animal I.D. | | Blood Glucose Level (mmol/L) | | | | | | Weight (g) | | | | | |
|---|---|---|---|---|---|---|---|---|---|---|---|---|---|
| | | | After Inducing | | | | | | After Inducing | | | | |
| | | Bef. Inducing | Day 1 | Day 6 | Day 14 | Day 21 | Day 28 | Bef. Inducing | Day 1 | Day 6 | Day 14 | Day 21 | Day 28 |
| Control | 1# | 6.4 | 26.7 | HI | HI | HI | HI | 362 | 358 | 340 | 369 | 343 | 354 |
| Group | 2# | 7.7 | 32.8 | 29.3 | HI | HI | HI | 392 | 352 | 332 | 306 | 307 | 310 |
| | 3# | 5.7 | HI | 28.7 | 33.2 | HI | HI | 392 | 362 | 358 | 372 | 380 | 384 |
| | 4# | 6.9 | HI | 31.6 | HI | HI | HI | 420 | 404 | 398 | 402 | 392 | 399 |
| | 5# | 7.2 | 27.2 | HI | HI | HI | HI | 406 | 385 | 380 | 364 | 353 | 361 |
| Test | 6# | 6.2 | 30.8 | HI | HI | HI | HI | 429 | 409 | 402 | 384 | 375 | 374 |
| Group | 7# | 6.8 | 33.1 | HI | HI | HI | HI | 422 | 344 | 328 | 344 | 314 | 326 |
| | 8# | 6.9 | 29.0 | HI | HI | HI | HI | 430 | 382 | 353 | 322 | 321 | 325 |
| | 9# | 5.1 | HI | 25.6 | 25.8 | HI | HI | 449 | 370 | 364 | 350 | 346 | 343 |
| | 10# | 7.6 | 28.2 | 32.8 | 31.6 | HI | HI | 432 | 407 | 375 | 348 | 325 | 327 |

TABLE 2-continued

| | Blood Glucose Level (mmol/L) | | | | | | Weight (g) | | | | | |
|---|---|---|---|---|---|---|---|---|---|---|---|---|
| | | After Inducing | | | | | | After Inducing | | | | |
| Animal I.D. | Bef. Inducing | Day 1 | Day 6 | Day 14 | Day 21 | Day 28 | Bef. Inducing | Day 1 | Day 6 | Day 14 | Day 21 | Day 28 |
| 11# | 7.1 | 30.6 | HI | HI | HI | HI | 388 | 370 | 359 | 342 | 359 | 364 |
| 12# | 7.1 | 32.6 | HI | HI | 27.7 | HI | 414 | 371 | 352 | 328 | 331 | 340 |

HI: >33.3 mmol/L

Table 2 shows the animal blood glucose level, which was measured using Ascensia® CONTOUR® Blood Glucose Meter, and the animal weight loss through the wound healing duration. After diabetic induction, 2 diabetic rats, deteriorated with significant weight loss (>20%) and excessive urination, had to be euthanized before the surgery.

E. Image Analysis

Figure 23:
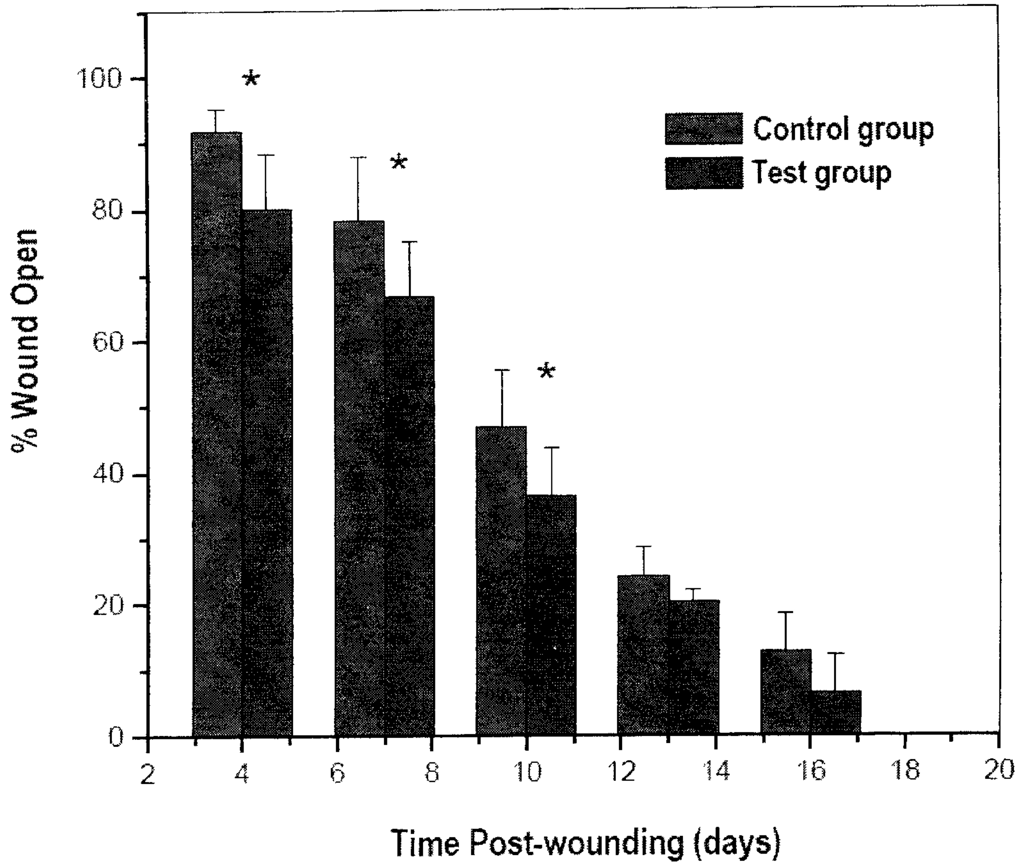
FIG. 23 compares the wound closure rate between control and test groups (*$p<0.05$).

The surface area of each lesion was quantified using Image-Pro Plus 5.0 software and plotted as a function of time. Using this software, the area of the open wounds was determined. The results are expressed in percentage of initial wound area as a function of times (FIG. 23). For each data point, means and standard deviation were calculated.

F. Statistical Analysis

All values in the text and figures were expressed as mean±standard error of the mean of n observations. Statistical analysis between experimental groups was performed using unpaired two-tailed Student's t tests. Statistical analysis between the right surgically divided and the left uninjured were performed using paired two-tailed Student's t tests. The confidence limit was predetermined at an alpha level of 0.05.

G. Assessment of Wound Healing

NO has been shown to be involved in the induction and up-regulation of vascular endothelial growth factor expression, which further encourages fibroblast and keratinocyte migration [34, 35]. The well-known antimicrobial and vasodilatory action of NO may also be important in the process of wound healing, particularly because vasodilation increases blood flow in the microvasculature, thus facilitating the delivery of both nutrients and cells to the site of injury.

Figure 24:
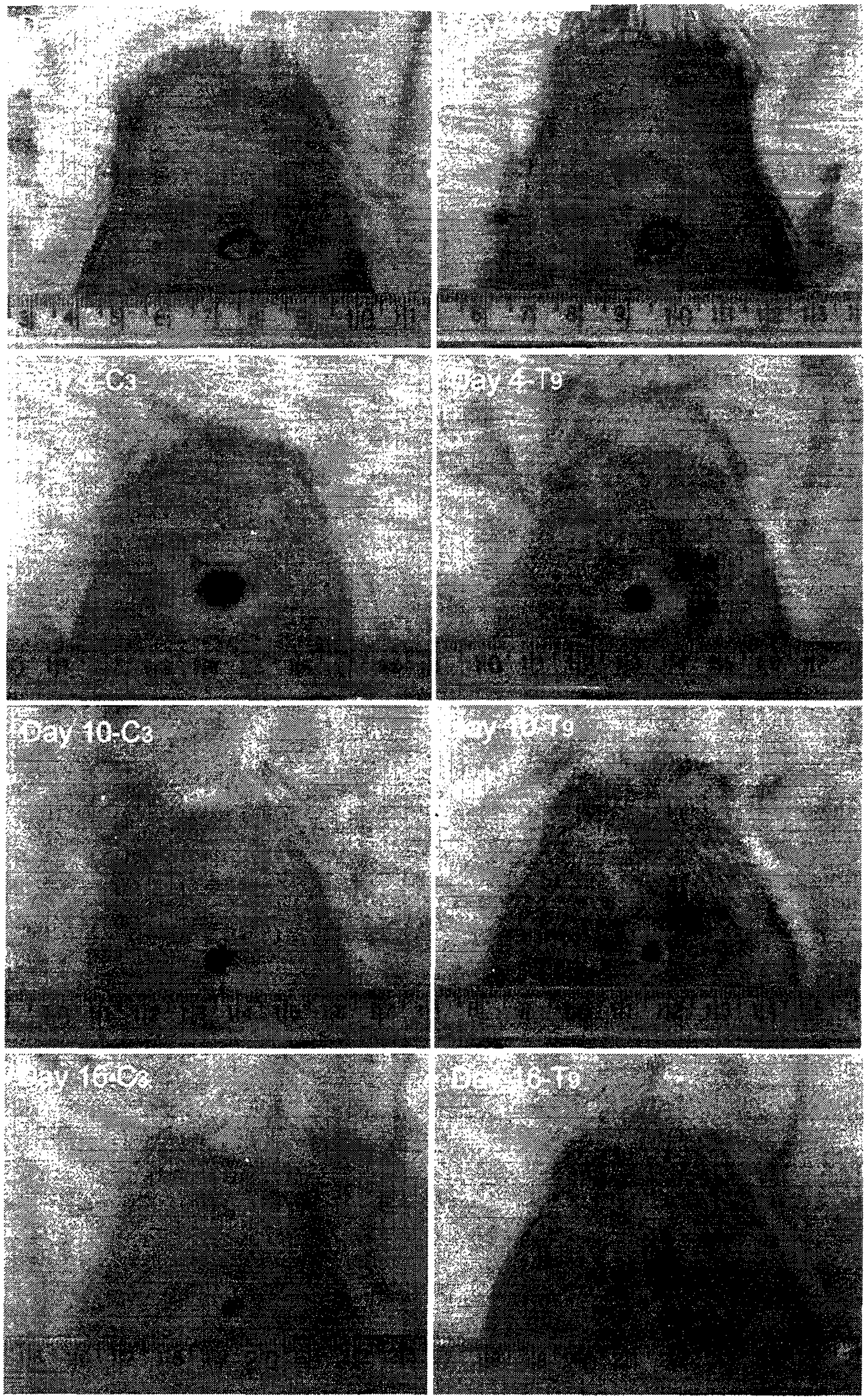
FIG. 24 presents photographs of wounds in control ($C_3$) and GSNO-treated ($T_9$) animals before and 4, 10, 16 days after wounding.

Results of FIG. 23 are promising as they demonstrate that topical application of the present NO-releasing supramacromolecular GSNO-PVMMA/PVP complex system can effectively accelerate wound closure ($p<0.05$). There is a statistically significant difference in wound closure tendency between the control and test group. Representative photographs of full thickness wounds for each group on days 0, 4, 10 and 16 are shown in FIG. 24. The apparent wound condition in terms of open area and granulation tissue also appears to be much better in the test group than in the control group on day 4, 10 and 16 after wounding.

Although this disclosure has described and illustrated certain preferred embodiments of the invention, it is to be understood that the invention is not restricted to those particular embodiments. Rather, the invention includes all embodiments which are functional or mechanical equivalence of the specific embodiments and features that have been described and illustrated.

The embodiments of the invention in which an exclusive property or privilege is claimed are defined as follows:

1. A bio-adhesive supramacromolecular complex of the general formula:

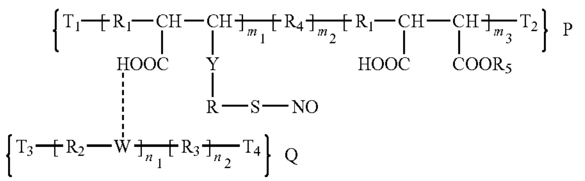

wherein $R_1$ is independently selected from the group consisting of alkanes unsubstituted or substituted with alkoxy groups; $R_2$ is independently selected from C1-6 alkyl; $R_3$ and $R_4$ are independently selected from the group consisting of substituted and unsubstituted aliphatic and aromatic alkyl; $R_5$ is independently selected from H or C1-6 alkyl; W is a hydrogen-bond accepting functional group-containing entity; Y is a carboxylic acid ester or amide linkage; R is an independently selected peptide linking group ; $T_1$, $T_2$, $T_3$ and $T_4$ are independently selected polymer residues; and $m_1$, $m_2$, $m_3$, $n_1$ and $n_2$ are integers selected from at least 25; and wherein P has a molecular weight of about $1\times10^3$ to $1\times10^7$ and Q has a molecular weight of about $1\times10^3$to $1\times10^7$.

2. A supramacromolecular complex as claimed in claim 1, wherein P is a maleic acid copolymer.

3. A supramacromolecular complex as claimed in claim 2, wherein said maleic acid copolymer is selected from the group consisting of poly(methyl vinyl ether-co-maleic acid) poly(vinyl pyrrolidone-co-dimethyl maleic acid), poly(ethylene-co-maleic acid), poly(isobutylene-co-maleic acid), poly (styrene-co-maleic acid), poly(ethylene-co-ethyl acrylate-co-maleic acid), poly(maleic acid-co-octadecene), polyethylene-graft-maleic anhydride, polypropylene-graft-maleic acid, and polyisoprene-graft-maleic acid.

4. A supramacromolecular complex as claimed in claim 1, wherein said $T_3$-$(R_2W.)_{n1}$-$(R_3)_{n2}$-$T_4$ is selected from the group consisting of poly(vinyl pyrrolidone), polyethylene glycol, poly(ethylene oxide), poly(vinyl pyrrolidone-co-vinyl acetate), polyethylene oxide-polypropylene oxide block copolymers (Pluronics or Polaxomers), polyethylene glycol fatty alcohol esters, polyethylene glycol fatty acids esters, ethyl cellulose, and chitosan.

5. A supramacromolecular complex as claimed in claim 4, wherein said $T_3$-$(R_2W.)_{n1}$-$(R_3)_{n2}$-$T_4$ is poly(vinyl pyrrolidone).

6. A supramacromolecular complex as claimed in claim 1, wherein Y.R, SNO is an amido-S-nitrosoglutathione or amido-phytochelatin.

7. A bio-adhesive supramacromolecular complex of the general formula:

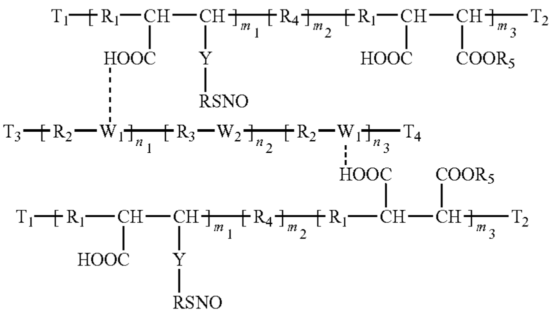

wherein $R_1$ is an alkyl vinyl ether ($C_1$-$C_5$), ethylene, propylene, isobutylene, butadiene, 1-octadecene, styrene, maleic acid, or maleic anhydride unit; $W_1$ and $W_2$ are hydrogen-bond accepting functional group-containing entities selected from vinylpyrrolidone, ethylene oxide, propylene oxide, vinyl acetate, alkoxyl substituted glucopyranose, glucosamine, and acetylglucosamine; $R_2$ and $R_3$ are independently selected from unsubstituted alkyl and substituted and unsubstituted aliphatic or aromatic alkyl; $R_4$ is a substituted aliphatic or aromatic alkyl; Y is a carboxylic acid ester or amide linkage; $R_5$ is independently selected from H and C1-6) alkyl; RSNO is a primary amine containing S-nitrosothiol of cysteine, γ-Glu-Cys, α-Glu-Cys, glutathione, homoglutathione, hydroxymethyl-glutathione, γ-Glu-Cys-Glu, α-Glu-Cys -Gly, α-Glu-Cys-β-Ala, α-Glu-Cys-Ser, αGlu-Cys-Glu, other glutathione analogs containing at least one of —SH and —$NH_2$ and —OH functional groups, and one of the following peptides: $(\gamma\text{Glu-Cys})_q$, $(\gamma\text{-Glu-Cys})_q$-Gly, $(\gamma\text{-Glu-Cys})_q$-β-Ala, $(\gamma\text{-Glu-Cys})_q$-Ser, $(\gamma\text{Glu-Cys})_q$Glu, $(\alpha\text{Glu-Cys})_q$,$(\alpha\text{-Glu-Cys})_q$Gly, $(\alpha\text{Glu-Cys})_q$-βAla, $(\alpha\text{Glu-Cys})_q$Ser, and$(\alpha\text{Glu-Cys})_q$ Glu, where q=2-11; $T_1$, $T_2$, $T_3$ and $T_4$ are independently selected polymer residues; $m_1$, $m_2$, $m_3$, $n_1$, $n_2$, and $n_3$ are integers greater than 25.

8. A suprarmacromolecular complex as claimed in claim 7, wherein $T_1$-[—$R_1$—CH(COOH)—CH(Y—RSNO)-$]_{m1}$-[—$R_4$—$]_{m2}$-[-$R_1$—CH(COOOC)CH—$]_{m3}$-$T_2$ is a reaction adduct of a primary amine containing S-nitrosothiols of claim 7 and a maleic anhydride polymer or copolymer.

9. A supramacromolecular complex as claimed in claim 8, wherein said maleic anhydride polymer or copolymer is selected from the group consisting of poly(methyl vinyl ether-alt-maleic anhydride), poly(maleic acid-co-maleic anhydride), poly(maleic anhydride), poly(vinylpyrrolidone-co-dimethyl maleic anhydride), poly(vinylacetate -co-maleic anhydride), poly(ethylene-alt-maleic anhydride), poly (isobutylene-alt-maleic anhydride), poly(styrene-alt-maleic anhydride), poly(ethylene-co-ethyl acrylate-co-maleic anhydride), and poly(maleic anhydride-alt-1-octadecene).

10. A supramacrornolecular complex as claimed in claim 8, wherein said nitric oxide donor RSNO is selected from the group consisting of S-nitrosothiol of cysteine, γ-Glu-Cys, α-Glu-Cys, glutathione, homoglutathione, hydroxymethyl-glutathione, γ-Glu-Cys-Glu, α-Glu-Cys-Gly,α-Glu-Cys-β-Ala, α-Glu-Cys-Ser, αGlu-Cys-Glu, other glutathione analogs containing at least one of —SH and —$NH_2$ and/or —OH functional groups, and one of the following peptides: $(\gamma\text{Glu-Cys})_q$, $(\gamma\text{-Glu-Cys})_q$-Gly, $(\gamma\text{-Glu-Cys})_q$-β-Ala, $(\gamma\text{-Glu-Cys})_q$-Ser, $(\gamma\text{Glu-Cys})_q$Glu, $(\alpha\text{-Glu-Cys})_q$,$(\alpha\text{-Glu-Cys})_q$Gly, $(\alpha\text{Glu-Cys})_q$-βAla, $(\alpha\text{Glu-Cys})_q$Ser, and$(\alpha\text{Glu-Cys})_q$-Glu, where q=2-11.

11. A supramacromolecular complex as claimed in claim 7, wherein said $T_g$-[-$R_2$-$W_1$-$]_{n1}$-[-$R_3$-$W_2$-$]_{n2}$-[-$R_2$-$W_1$-]$n_3$-$T_4$ is selected from the group consisting of poly(vinyl pyrroildone), polyethylene glycol, poly(ethylene oxide), poly(vinyl pyrrolidone-co-vinyl acetate), polyethylene oxide- polypropylene oxide block copolymers (Pluronics and Polaxomers), polyethylene glycol fatty alcohols, and polyethylene glycol fatty acids esters, ethyl cellulose, and chitosan.

12. A supramacromolecular complex as claimed in claim 11, wherein said $T_3$-[-$R^2W_1$-$]_{n1}$-[-$R_3$-$W^2$-$]_{n2}$-[$R_2$-$W_1]_{n3}T_4$ is poly(vinyl pyrrolidone).

13. A supramacromolecular complex as claimed in claim 7, wherein Y—RSNO is an amido-S-nitrosoglutathione or amido-phytochelatin.

14. A pharmaceutical composition comprising an effective, wound healing amount of said supramatromolecular complex as claimed in claim 7 and a physiological acceptable carrier.

15. A method of preparing a layer-by-layer assemblies coating containing a nitric oxide suprarmacromolecular complex as claimed in claim 7 or a pharmaceutically acceptable composition comprising an effective wound healing amount of said complex and a physiological carrier, comprising:

(i) covalently linking a S-nitroso compound having an amino linking group with a bio-adhesive, hydrophobic polyanhydride compound to form a nitric oxide donor polymeric carrier; and (ii) alternatingly depositing said carrier and an intermolecular hydrogen bond-acceptable polymer from solution to form highly interdigitated thin layers joined by strong hydrogen bonding interactions.

16. A method of preparing nanofibers containing a supramacromolecular complex as claimed in claim 7 or a pharmaceutically acceptable composition comprising an effective wound healing amount of said complex and a physiological carrier, comprising;

(i) covalently linking a S-nitroso compound having an amino linking group with a bio-adhesive, hydrophobic polyanhydride compound to form a nitric oxide donor polymeric carrier; and (ii) mixing said carrier with an intermolecular hydrogen bond-acceptable polymer to produce said polymeric blend mixture (iii) spinning this concentrated blend system in a high voltage field to produce continuous nanofibers which can be (iv) deposited on a plate collector to form a nonwoven mat or (v) deposited on a roil collector to form a coating.

17. A method of preparing microspheres containing a supramacromolecular complex as claimed in claim 7 or a pharmaceutically acceptable composition comprising an effective wound healing amount of said complex and a physiological carrier, comprising:

(i) covalently linking a S-nitroso compound having an amino linking group with a bio-adhesive, hydrophobic polyanhydride compound to form a nitric oxide donor polymeric carrier; and (ii) mixing said carrier with a hydrogen bond-acceptable polymer to produce said polymeric blend mixture (iii) spraying a solution of this polymer blend in a high voltage field using an ultrasonic atomizer apparatus to produce microspheres which can be (iv) collected after drying or (v) deposit on a roll device to form a coating.

18. A method of enhancing the healing of a skin wound or infection comprising applying to a wound or substrate an effective wound or infection healing amount of a supramacromolecular complex as claimed in claim 7 or a pharmaceutically acceptable composition comprising an effective wound healing amount of said complex and a physiological carrier.

* * * * *